United States Patent
Iwase et al.

(10) Patent No.: US 10,023,554 B2
(45) Date of Patent: *Jul. 17, 2018

(54) HALOGEN-SUBSTITUTED HETEROCYCLIC COMPOUND SALT

(71) Applicant: UBE INDUSTRIES, LTD., Ube-shi, Yamaguchi (JP)

(72) Inventors: Noriaki Iwase, Ube (JP); Hiroshi Nishida, Ube (JP); Makoto Okudo, Ube (JP); Masaaki Ito, Ube (JP); Shigeyuki Kono, Ube (JP); Masaaki Matoyama, Ube (JP); Shigeru Ushiyama, Ube (JP); Eiji Okanari, Ube (JP); Hirofumi Matsunaga, Ube (JP); Kenji Nishikawa, Ube (JP); Tomio Kimura, Tokyo (JP)

(73) Assignee: UBE INDUSTRIES, LTD., Ube-Shi, Yamaguchi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/321,633

(22) PCT Filed: Jun. 26, 2015

(86) PCT No.: PCT/JP2015/068575
§ 371 (c)(1),
(2) Date: Dec. 22, 2016

(87) PCT Pub. No.: WO2015/199234
PCT Pub. Date: Dec. 30, 2015

(65) Prior Publication Data
US 2017/0158663 A1    Jun. 8, 2017

(30) Foreign Application Priority Data
Jun. 27, 2014  (JP) ................. 2014-132413

(51) Int. Cl.
*C07D 333/36*     (2006.01)
(52) U.S. Cl.
CPC .................. *C07D 333/36* (2013.01)
(58) Field of Classification Search
CPC .............................................. C07D 333/36
USPC ....................................................... 549/59
See application file for complete search history.

(56) References Cited

U.S. PATENT DOCUMENTS

| | | | |
|---|---|---|---|
| 2003/0114505 A1 | 6/2003 | Ueno et al. | |
| 2004/0067908 A1 | 4/2004 | Nakade et al. | |
| 2006/0194850 A1 | 8/2006 | Yamamoto et al. | |
| 2009/0170911 A1 | 7/2009 | Yamamoto et al. | |
| 2010/0152257 A1 | 6/2010 | Hutchinson et al. | |
| 2011/0196005 A1 | 8/2011 | Hutchinson et al. | |
| 2011/0301142 A1 | 12/2011 | Hutchinson et al. | |
| 2011/0301211 A1 | 12/2011 | Hutchinson et al. | |
| 2012/0258987 A1 | 10/2012 | Seiders et al. | |

(Continued)

FOREIGN PATENT DOCUMENTS

| | | |
|---|---|---|
| WO | WO 01/60819 A1 | 8/2001 |
| WO | WO 02/062389 A1 | 8/2002 |

(Continued)

OTHER PUBLICATIONS

Stoddard; Biomolecules & Therapeutics 2015, 23, 1-11.*
Castelino et al., "Amelioration of Dermal Fibrosis by Genetic Deletion or Pharmacologic Antagonism of Lysophosphatidic Acid Receptor 1 in a Mouse Model of Scleroderma", Arthritis & Rheumatism, May 2011, vol. 63, No. 5, pp. 1405-1415.
Gräler et al., "Lysophospholipids and their G protein-coupled receptors in inflammation and immunity", Biochimica et Biophysica Acta, 2002, vol. 1582, pp. 168-174.
Guo et al., "Mitogenic Signaling in Androgen Sensitive and Insensitive Prostate Cancer Cell Lines", The Journal of Urology, Mar. 2000, vol. 163, pp. 1027-1032.

(Continued)

*Primary Examiner* — Daniel R Carcanague
(74) *Attorney, Agent, or Firm* — Birch, Stewart, Kolasch & Birch, LLP

(57) ABSTRACT

The invention provides a novel α-halogen-substituted thiophene compound salt that has a potent LPA receptor antagonistic action and is useful as a medicament.
The salt is represented by the general formula (I):

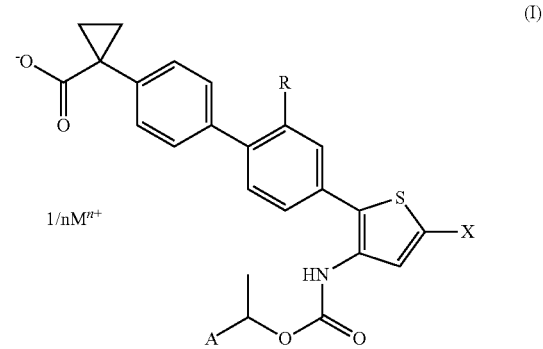

(wherein R is a hydrogen atom or a methoxy group; X is a halogen atom; A is selected from the group consisting of:

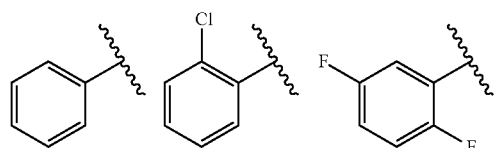

(Continued)

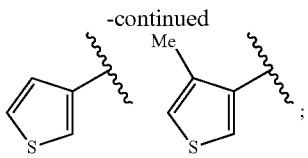

M is an alkali metal or an alkaline earth metal; and n is 1 when M is an alkali metal and is 2 when M is an alkaline earth metal).

15 Claims, No Drawings

(56) References Cited

U.S. PATENT DOCUMENTS

| | | |
|---|---|---|
| 2013/0041000 A1 | 2/2013 | Yamamoto et al. |
| 2013/0072449 A1 | 3/2013 | Buckman et al. |
| 2013/0253004 A1 | 9/2013 | Seiders et al. |
| 2015/0376160 A1 | 12/2015 | Iwase et al. |

FOREIGN PATENT DOCUMENTS

| | | | |
|---|---|---|---|
| WO | WO 2005/012269 A1 | 2/2005 | |
| WO | WO 2010/077882 A2 | 7/2010 | |
| WO | WO 2010/077883 A2 | 7/2010 | |
| WO | WO 2010/141761 A2 | 12/2010 | |
| WO | WO 2010/141768 A2 | 12/2010 | |
| WO | WO 2011/017350 A2 | 2/2011 | |
| WO | WO 2011/041461 A2 | 4/2011 | |
| WO | WO 2011/041462 A2 | 4/2011 | |
| WO | WO 2011/041694 A2 | 4/2011 | |
| WO | WO 2011/041729 A2 | 4/2011 | |
| WO | WO 2011/091167 A2 | 7/2011 | |
| WO | WO 2011/159632 A1 | 12/2011 | |
| WO | WO 2011/159633 A1 | 12/2011 | |
| WO | WO 2011/159635 A1 | 12/2011 | |
| WO | WO 2012/078593 A2 | 6/2012 | |
| WO | WO 2012/078805 A1 | 6/2012 | |
| WO | WO 2012/138648 A1 | 10/2012 | |
| WO | WO 2012/138797 A1 | 10/2012 | |
| WO | WO 2013/025733 A1 | 2/2013 | |
| WO | WO 2013/085824 A1 | 6/2013 | |
| WO | WO 2013/189862 A1 | 12/2013 | |
| WO | WO 2013/189864 A1 | 12/2013 | |
| WO | WO 2013/189865 A1 | 12/2013 | |
| WO | WO 2014/104372 A1 | 7/2014 | |
| WO | WO 2017086430 | * | 5/2017 |

OTHER PUBLICATIONS

Ikeda et al., "Effects of Lysophosphatidic Acid on Proliferation of Stellate Cells and Hepatocytes in Culture", Biochemical and Biophysical Research Communications, 1998, vol. 248, No. 2, pp. 436-440.

Imamura et al., "Induction of In Vitro Tumor Cell Invasion of Cellular Monolayers by Lysophosphatidic Acid or Phospholipase D", Biochemical and Biophysical Research Communications, Jun. 15, 1993, vol. 193, No. 2, pp. 497-503.

Inoue et al., "Initiation of neuropathic pain requires lysophosphatidic acid receptor signaling", Nature Medicine, Jul. 2004, vol. 10, No. 7, pp. 712-718.

International Search Report, issued in PCT/JP2015/068575 (PCT/ISA/210), dated Oct. 6, 2015.

Pradère et al., "LPA1 Receptor Activation Promotes Renal Interstitial Fibrosis", Journal of the American Society of Nephrology, 2007, vol. 18, pp. 3110-3118.

Qian et al., "Discovery of Highly Selective and Orally Active Lysophosphatidic Acid Receptor-1 Antagonists with Potent Activity on Human Lung Fibroblasts", Journal of Medicinal Chemistry, 2012, vol. 55, pp. 7920-7939.

Swaney et al., "A novel, orally active LPA1 receptor antagonist inhibits lung fibrosis in the mouse bleomycin model", British Journal of Pharmacology, 2010, vol. 160, pp. 1699-1713.

Swaney et al., "Pharmacokinetic and Pharmacodynamic Characterization of an Oral Lysophosphatidic Acid Type 1 Receptor-Selective Antagonist", The Journal of Pharmacology and Experimental Therapeutics, 2011, vol. 336, No. 3, pp. 693-700.

Tager et al., "The lysophosphatidic acid receptor LPA1 links pulmonary fibrosis to lung injury by mediating fibroblast recruitment and vascular leak", Nature Medicine, Jan. 2008, vol. 14, No. 1, pp. 45-54.

Tangkijvanich et al., "Rho and p38 MAP Kinase Signaling Pathways Mediate LPA-Stimulated Hepatic Myofibroblast Migration", Journal of Biomedical Science 2003, vol. 10, pp. 352-358.

Xu et al., "Lysophospholipids activate ovarian and breast cancer cells", Biochemical Journal, 1995, vol. 309, pp. 933-940.

Yanase et al., "Lysophosphatidic Acid Enhances Collagen Gel Contraction by Hepatic Stellate Cells: Association with Rho-Kinase", Biochemical and Biophysical Research Communications, 2000, vol. 277, No. 1, pp. 72-78.

Zhao et al., "Regulation of Lysophosphatidic Acid Receptor Expression and Function in Human Synoviocytes: Implications for Rheumatoid Arthritis?", Molecular Pharmacology, 2008, vol. 73, No. 2, pp. 587-600.

Zhou et al., "Phosphatidic Acid and Lysophosphatidic Acid Induce Haptotactic Migration of Human Monocytes", The Journal of Biological Chemistry, 1995, vol. 270, No. 43, pp. 25549-25556.

* cited by examiner

HALOGEN-SUBSTITUTED HETEROCYCLIC COMPOUND SALT

TECHNICAL FIELD

The present invention relates to a novel α-halogen-substituted thiophene compound salt useful as a medicament. The α-halogen-substituted thiophene compound salt of the present invention has a lysophosphatidic acid (LPA) receptor antagonistic action and is hence useful for the prevention and/or the treatment of diseases induced by LPA.

BACKGROUND ART

Lysophosphatidic acid (LPA) is a physiologically active phospholipid which is present in a living body. By binding to specific G-protein-coupled receptors (LPA1, LPA2, LPA3, LPA4, LPA5 and LPA6), LPA transduces signals into cells and modulates the proliferation, the differentiation, the survival, the migration, the adhesion, the infiltration and the morphogenesis of cells. Further, it is known that LPA is involved in diseases accompanied with fibrosis in various organs.

It has been reported that in the liver, LPA stimulates the proliferation or contraction of stellate cells which play an important role in the process of hepatic fibrosis, and stimulates the migration of myofibroblasts (see Non-Patent Documents 1, 2 and 3).

It has been reported that in the kidney, the production of LPA or the expression of LPA1 is enhanced in mice with unilateral ureteral ligation as renal fibrosis animal models, and that the renal fibrosis is suppressed by LPA1 deficiency or administered of an LPA receptor antagonist (see Non-Patent Documents 4 and 5).

Regarding the lung, it has been reported that bronchoalveolar lavage fluids from patients with idiopathic pulmonary fibrosis have an increased LPA concentration, and that LPA1 is most expressed receptor in fibroblasts having an important role in the process of pulmonary fibrosis and LPA induces the migration of fibroblasts. Further, it has been reported that the LPA1 deficiency or the administration of an LPA receptor antagonist suppresses fibrosis in intratracheally bleomycin administered mice as pulmonary fibrosis animal models (see Non-Patent Documents 6 and 7).

Concerning the skin, it has been reported that skin fibrosis is suppressed by the LPA1 deficiency or the administration of an LPA receptor antagonist in mice which are subcutaneously administered with bleomycin as scleroderma models (see Non-Patent Document 8).

It is also known that LPA is involved in immunological or inflammatory diseases. It has been reported that LPA stimulates the migration of human monocyte, and is involved in the proliferation or infiltration of T cells. Further, it has been reported that synovial cells of rheumatoid arthritis patients express LPA receptors and migrate or produce IL-6 and IL-8 by LPA stimulation, and that these actions are inhibited by an LPA receptor antagonist (see Non-Patent Documents 9, 10 and 11).

In addition, it has been reported that LPA and LPA1 are involved in the development of neuropathic pain (see Patent Document 12), that LPA causes extracted urethra specimens and prostatic specimens to contract and the intraurethral pressure to increase and is thus involved in urologic diseases (see Patent Document 1), and that LPA is involved in cancer-related diseases by stimulating the infiltration of cancer cells, by stimulating the proliferation of ovary cancer cells, or by stimulating the proliferation of prostate cancer cells (see Non-Patent Documents 13, 14 and 15).

Based on these reports, a medicament that antagonizes the LPA receptors (in particular, the LPA1 receptor) is considered to be useful for the prevention and/or the treatment of diseases accompanying fibrosis, immunological or inflammatory diseases, central or peripheral nervous system diseases, urologic diseases and cancer-related diseases, etc.

On the other hand, Patent Documents 2 to 23 and Non-Patent Documents 5, 7, 8 and 16 disclose ([1,1'-biphenyl]-4-yl)acetic acid derivatives, Patent Document 17 discloses (2'-methoxy-[1,1'-biphenyl]-4-yl)acetic acid derivatives, and Patent Document 19 discloses 3-chloroisothiazole derivatives as compound having an antagonistic function on LPA receptors, there is no disclosure of the compounds according to the present invention.

PRIOR ART DOCUMENTS

Patent Documents

Patent Document 1: WO 2002/062389
Patent Document 2: WO 2010/077882
Patent Document 3: WO 2010/077883
Patent Document 4: WO 2010/141761
Patent Document 5: WO 2010/141768
Patent Document 6: WO 2011/017350
Patent Document 7: WO 2011/041461
Patent Document 8: WO 2011/041462
Patent Document 9: WO 2011/041694
Patent Document 10: WO 2011/041729
Patent Document 11: WO 2011/091167
Patent Document 12: WO 2011/159632
Patent Document 13: WO 2011/159633
Patent Document 14: WO 2011/159635
Patent Document 15: WO 2012/078593
Patent Document 16: WO 2012/078805
Patent Document 17: WO 2012/138648
Patent Document 18: WO 2012/138797
Patent Document 19: WO 2013/025733
Patent Document 20: WO 2013/085824
Patent Document 21: WO 2013/189862
Patent Document 22: WO 2013/189864
Patent Document 23: WO 2013/189865

Non-Patent Documents

Non-Patent Document 1: Biochemical and Biophysical Research Communications, 248(1998) 436-440
Non-Patent Document 2: Biochemical and Biophysical Research Communications, 277 (2000) 72-78
Non-Patent Document 3: Journal of Biomedical Science, 10 (2003) 352-358
Non-Patent Document 4: Journal of the American Society of Nephrology, 18 (2007) 3110-3118
Non-Patent Document 5: The Journal of Pharmacology and Experimental Therapeutics, 336 (2011) 693-700
Non-Patent Document 6: Nature Medicine, 14 (2008) 45-54
Non-Patent Document 7: British Journal of Pharmacology, 160 (2010) 1699-1713
Non-Patent Document 8: Arthritis & Rheumatism, 63(2011) 1405-1415
Non-Patent Document 9: Journal of Biological Chemistry, 270 (1995) 25549-25556
Non-Patent Document 10: Biochimica et Biophysica Acta, 1582 (2002) 168-174

Non-Patent Document 11: Molecular Pharmacology, 73 (2008) 587-600
Non-Patent Document 12: Nature Medicine, 10 (2004) 712-718
Non-Patent Document 13: Biochemical and Biophysical Research Communications, 193 (1993) 497-503
Non-Patent Document 14: Biochemical Journal, 309 (1995) 933-940
Non-Patent Document 15: The Journal of Urology, 163 (2000) 1027-1032
Non-Patent Document 16: Journal of Medicinal Chemistry, 55 (2012) 7920-7939

DISCLOSURE OF THE INVENTION

Problems to be Solved by the Invention

The present inventors carried out researches on various halogen-substituted heterocyclic compound salts in order to develop a excellent medicament for the treatment or the prevention of diseases accompanying fibrosis, immunological or inflammatory diseases, central or peripheral nervous system diseases, urologic diseases and cancer-related diseases, etc. As a result, the present inventors have found that a novel α-halogen-substituted thiophene compound salt having a specific structure exhibits an excellent LPA receptor antagonistic action and is useful as a medicament (in particular, for the prevention and/or the treatment of diseases accompanying fibrosis, immunological or inflammatory diseases, central or peripheral nervous system diseases, urologic diseases and cancer-related diseases). The present invention has been completed based on the finding.

The present invention provides a novel α-halogen-substituted thiophene compound salt which has a potent LPA receptor-antagonistic action and is useful as a medicament for the treatment and/or the prevention (preferably, a medicament for the treatment) of, in particular, diseases accompanying by fibrosis, immunological or inflammatory diseases, central or peripheral nervous system diseases, urologic diseases and cancer-related diseases.

Means for Solving the Problems

The present invention provides:
(1) A salt represented by the general formula (I):

[Chem. 1]

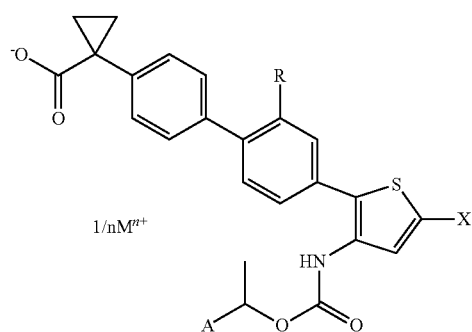

(wherein
R is a hydrogen atom or a methoxy group,
X is a halogen atom,
A is selected from the group consisting of:

[Chem. 2]

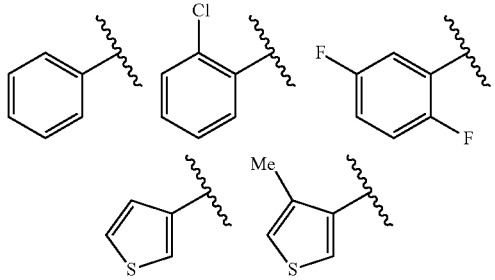

M is an alkali metal or an alkaline earth metal, and
n is 1 when M is an alkali metal and is 2 when M is an alkaline earth metal).

(2) The salt according to (1), wherein the alkali metal or the alkaline earth metal is sodium, potassium or calcium.

(3) A salt of (R)-1-[4'-(5-chloro-3-{[(1-phenylethoxy)carbonyl]amino}thiophen-2-yl)-2'-methoxy-[1,1'-biphenyl]-4-yl]cyclopropanecarboxylic acid with an alkali metal or an alkaline earth metal.

(4) The salt according to (3), wherein the alkali metal or the alkaline earth metal is sodium, potassium or calcium.

(5) A salt of (R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylic acid with an alkali metal or an alkaline earth metal.

(6) The salt according to (5), wherein the alkali metal or the alkaline earth metal is sodium, potassium or calcium.

(7) A salt of (R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylic acid with an alkali metal or an alkaline earth metal.

(8) The salt according to (7), wherein the alkali metal or the alkaline earth metal is sodium, potassium or calcium.

(9) A salt of (R)-1-{4'-[5-chloro-3-({[1-(thiophen-3-yl)ethoxy]carbonyl}amino)thiophen-2-yl]-[1,1'-biphenyl]-4-yl}cyclopropanecarboxylic acid with an alkali metal or an alkaline earth metal.

(10) The salt according to (9), wherein the alkali metal or the alkaline earth metal is sodium, potassium or calcium.

(11) A salt of (R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylic acid with an alkali metal or an alkaline earth metal.

(12) The salt according to (11), wherein the alkali metal or the alkaline earth metal is sodium, potassium or calcium.

(13) An LPA receptor antagonist comprising the salt according to any of (1) to (12) as an active ingredient.

(14) A pharmaceutical composition comprising the salt according to any of (1) to (12) as an active ingredient.

(15) The pharmaceutical composition according to (14) for the treatment or the prevention of a disease accompanying fibrosis, an immunological or inflammatory disease, a central or peripheral nervous system disease, a urologic disease or a cancer-related disease.

Specific examples of the compounds represented by the general formula (I) of the present invention include compounds described in Table 1 below. In Table 1, OMe represents a methoxy group, and "Racemic" and "(R)-" represent the configuration of the carbon atom marked with "*" in the general formula (I) below.

[Chem. 3]

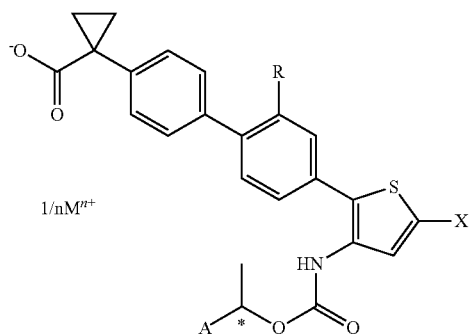

TABLE 1

| Compound No. | R | X | A | M | n | Configuration |
|---|---|---|---|---|---|---|
| I-1 | OMe | Cl | Phenyl | Na | 1 | racemic |
| I-2 | OMe | Cl | Phenyl | Na | 1 | (R)- |
| I-3 | OMe | Cl | Phenyl | K | 1 | racemic |
| I-4 | OMe | Cl | Phenyl | K | 1 | (R)- |
| I-5 | OMe | Cl | Phenyl | Ca | 2 | racemic |
| I-6 | OMe | Cl | Phenyl | Ca | 2 | (R)- |
| I-7 | OMe | Cl | 2,5-Difluorophenyl | Na | 1 | racemic |
| I-8 | OMe | Cl | 2,5-Difluorophenyl | Na | 1 | (R)- |
| I-9 | OMe | Cl | 2,5-Difluorophenyl | K | 1 | racemic |
| I-10 | OMe | Cl | 2,5-Difluorophenyl | K | 1 | (R)- |
| I-11 | OMe | Cl | 2,5-Difluorophenyl | Ca | 2 | racemic |
| I-12 | OMe | Cl | 2,5-Difluorophenyl | Ca | 2 | (R)- |
| I-13 | OMe | F | 2-Chlorophenyl | Na | 1 | racemi |
| I-14 | OMe | F | 2-Chlorophenyl | Na | 1 | (R)- |
| I-15 | OMe | F | 2-Chlorophenyl | K | 1 | racemic |
| I-16 | OMe | F | 2-Chlorophenyl | K | 1 | (R)- |
| I-17 | OMe | F | 2-Chlorophenyl | Ca | 2 | racemic |
| I-18 | OMe | F | 2-Chlorophenyl | Ca | 2 | (R)- |
| I-19 | H | Cl | Thiophen-3-yl | Na | 1 | racemic |
| I-20 | H | Cl | Thiophen-3-yl | Na | 1 | (R)- |
| I-21 | H | Cl | Thiophen-3-yl | K | 1 | racemic |
| I-22 | H | Cl | Thiophen-3-yl | K | 1 | (R)- |
| I-23 | H | Cl | Thiophen-3-yl | Ca | 2 | racemic |
| I-24 | H | Cl | Thiophen-3-yl | Ca | 2 | (R)- |
| I-25 | H | F | 4-Methylthiophen-3-yl | Na | 1 | racemic |
| I-26 | H | F | 4-Methylthiophen-3-yl | Na | 1 | (R)- |
| I-27 | H | F | 4-Methylthiophen-3-yl | K | 1 | racemic |
| I-28 | H | F | 4-Methylthiophen-3-yl | K | 1 | (R)- |
| I-29 | H | F | 4-Methylthiophen-3-yl | Ca | 2 | racemic |
| I-30 | H | F | 4-Methylthiophen-3-yl | Ca | 2 | (R)- |

Effects of Invention

The α-halogen-substituted thiophene compound salts of the present invention that are represented by the general formula (I) have a potent LPA receptor antagonistic action and are hence useful as medicaments for the prevention and/or the treatment of diseases accompanying fibrosis, immunological or inflammatory diseases, central or peripheral nervous system diseases, urologic diseases and cancer-related diseases.

MODE FOR CARRYING OUT THE INVENTION

Preferred embodiments of each substituent group in the salts represented by the general formula (I) will be described below.

Examples of the "halogen atoms" represented by X include a fluorine atom, a chlorine atom, a bromine atom and an iodine atom.

Preferably, the "halogen atom" represented by X is a fluorine atom, a chlorine atom or a bromine atom, and is more preferably a fluorine atom or a chlorine atom.

Examples of the "alkali metals" represented by M include lithium, sodium, potassium, rubidium and cesium, with sodium and potassium being preferable.

Examples of the "alkaline earth metals" represented by M include magnesium, calcium, strontium and barium, with calcium being preferable.

In a case where the salts of the present invention represented by the general formula (I) have optical isomers, geometric isomers and rotational isomers, these isomers are within the scope of the present invention. Further, in a case where proton tautomerism is present, these tautomers are also within the scope of the present invention.

In the general formula (I), the group represented by:

[Chem. 4]

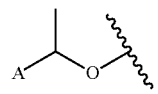

is preferably the following group:

[Chem. 5]

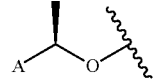

The salts of the invention represented by the general formula (I) may form hydrates or solvates, of which each and mixtures are also within the scope of the invention.

One or more kinds of the atoms constituting the salts of the present invention represented by the formula (I) may have atomic isotopes in an unnatural proportion. Examples of the atomic isotopes include deuterium ($^2H$), tritium ($^3H$), carbon-14 ($^{14}C$), fluorine-18 ($^{18}F$), sulfur-35 ($^{35}S$) and iodine-125 ($^{125}I$). Such compounds are useful as treatment or preventive medicaments, research reagents such as assay reagents, and diagnostic agents such as in vivo diagnostic imaging agents. All the isotopic variants of the salts of the invention represented by the formula (I) are within the scope of the present invention irrespective of whether or not they are radioactive.

A general process for producing the compound of the present invention is shown below. Each specific process for producing the compound of the present invention will be individually described in detail in Examples later.

[Chem. 6]

Step 1

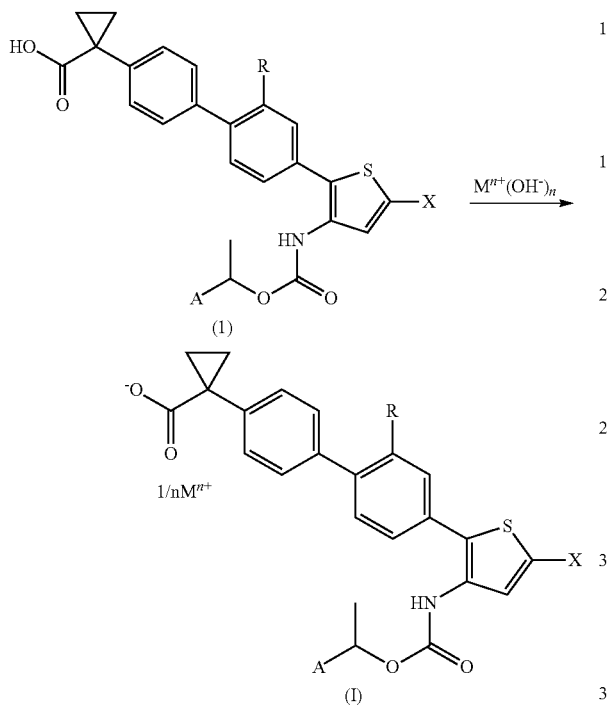

[Chem. 7]

Step 2

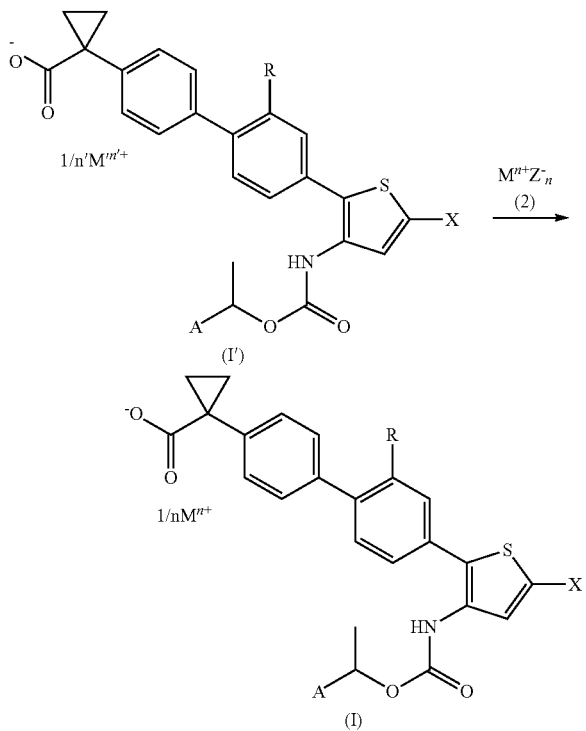

[Chem. 8]

Step 3

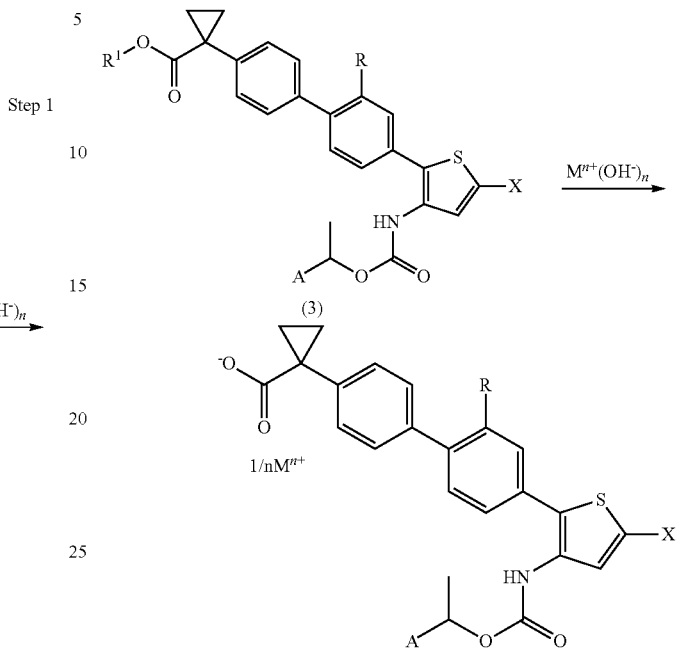

(In the formulae, R, X, A, M and n are the same as defined hereinabove, M' and n' have the same definitions as M and n, respectively, $Z^-$ is an anion such as a hydroxide ion, a halide ion or an acetate ion, and $R^1$ is a carboxylic acid-protecting group such as an alkyl group that is deprotected by hydrolysis.)

The salts of the present invention represented by the general formula (I) may be synthesized by any of the steps 1 to 3 described above.

In reaction in each of steps 1 to 18 described below, any solvent may be used without limitation as long as the solvent does not inhibit the reaction and can dissolve part of starting raw materials. Examples of the solvents include aliphatic hydrocarbons such as hexane, pentane, heptane, petroleum ethers and cyclohexane; aromatic hydrocarbons such as benzene, toluene, xylene and ethylbenzene; halogenated hydrocarbons such as dichloromethane, chloroform, carbon tetrachloride, dichloroethane, chlorobenzene and dichlorobenzene; ethers such as diethyl ether, diisopropyl ether, tetrahydrofuran, 2-methyltetrahydrofuran, 1,4-dioxane, dimethoxyethane and diethylene glycol dimethyl ether; ketones such as acetone, methyl ethyl ketone, methyl isobutyl ketone and cyclohexanone; esters such as methyl acetate, ethyl acetate, propyl acetate, isopropyl acetate and butyl acetate; nitriles such as acetonitrile, propionitrile, butyronitrile and isobutyronitrile; carboxylic acids such as acetic acid and propionic acid; alcohols such as methanol, ethanol, 1-propanol, 2-propanol, 1-butanol, 2-butanol, 2-methyl-1-propanol, 2-methyl-2-propanol and 1,2-propanediol; amides such as formamide, N,N-dimethylformamide, N,N-dimethylacetamide, 1-methyl-2-pyrrolidone, dimethylimidazolone and hexamethylphosphorotriamide; sulfoxides such as dimethylsulfoxide; sulfones such as sulfolane; water; and a mixed solvent thereof.

In the reaction in each of the steps 1 to 18 described below, the reaction temperature is variable depending on conditions such as solvents, starting raw materials and reagents, and the reaction time is variable depending on conditions such as solvents, starting raw materials, reagents and reaction temperatures.

Step 1: Compound (1) may be reacted in a reaction solvent using an alkali metal or alkaline earth metal hydroxide to synthesize a salt of the general formula (I).

The reaction solvent is preferably water or a water/organic solvent mixture, and is more preferably water, acetonitrile/water mixture, or acetonitrile/tetrahydrofuran/water mixture.

Step 2: Compound (I') and Compound (2) may be subjected to base exchange in a reaction solvent to synthesize a salt of the general formula (I).

The reaction solvent is preferably water or a water/organic solvent mixture, and is more preferably water or acetonitrile/water mixture.

Step 3: Compound (3) may be hydrolyzed in a reaction solvent using an alkali metal or alkaline earth metal hydroxide to synthesize a salt of the general formula (I).

The reaction solvent is preferably water or a water/organic solvent mixture, and is more preferably 2-propanol/water mixture or 2-propanol/tetrahydrofuran/water mixture.

A general process for producing a synthetic intermediate of the compound of the present invention will be described below. Each specific process for producing the synthetic intermediate of the compound of the present invention will be individually described in detail in Examples later.

In the synthetic routes illustrated below, R, X, A, M, M', n, n', Z⁻ and R¹ have the same meanings as described above. L, L$^a$ and Q are substituents necessary for the coupling reaction, and for example, in case where L or L$^a$ is a chlorine atom, a bromine atom, an iodine atom or a trifluoromethanesulfonyloxy group, etc., Q is boronic acid, a boronate ester or a trialkyltin, etc., and in case where L or L$^a$ is boronic acid, a boronate ester or a trialkyltin, etc., Q is a chlorine atom, a bromine atom, an iodine atom or a trifluoromethanesulfonyloxy group, etc.

[Chem. 9]

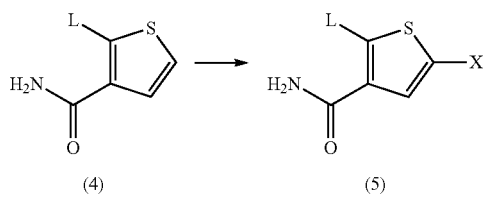

Step 4: In accordance with a method described in, for example, Tetrahedron, 64 (2008), pp. 9733-9737 or Bioorganic and Medicinal Chemistry Letters, 21 (2011), pp. 528-530, Compound (4) may be halogenated with a halogenating agent in a reaction solvent to synthesize Compound (5).

Preferred examples of the reaction solvents include aliphatic hydrocarbons, halogenated hydrocarbons, ethers, nitriles, carboxylic acids, amides, sulfoxides, water and a mixed solvent thereof. N,N-dimethylformamide is more preferable.

Examples of the halogenating agents include iodine, N-iodosuccinimide, bromine, N-bromosuccinimide, 1,2-dibromoethane, 1,2-dibromo-1,1,2,2-tetrafluoroethane, chlorine, N-chlorosuccinimide, xenon difluoride, N-fluorobenzenesulfonimide and N-fluoro-N'-(chloromethyl)triethylenediamine bis(tetrafluoroborate).

Alternatively, Compound (4) may be converted to an anion in a reaction solvent using a base and subsequently treated with a halogenating agent to synthesize Compound (5) in accordance with a method described in, for example, Tetrahedron Letters, 51 (2010), pp. 4526-4529 or Journal of Medicinal Chemistry, 54 (2011), pp. 2687-2700.

Preferred examples of the reaction solvents include aliphatic hydrocarbons, aromatic hydrocarbons, halogenated hydrocarbons, ethers and a mixed solvent thereof. Ethers, aliphatic hydrocarbons and a mixed solvent thereof are more preferable.

Examples of the bases include alkyllithiums such as n-butyllithium, sec-butyllithium and tert-butyllithium; lithium amides such as lithium diisopropylamide and lithium 2,2,6,6-tetramethylpiperidide; Grignard reagents such as ethylmagnesium bromide, ethylmagnesium chloride, isopropylmagnesium chloride and phenylmagnesium chloride; magnesium amides such as magnesium chloride diisopropylamide and magnesium chloride 2,2,6,6-tetramethylpiperidine; and disilazane bases such as lithium 1,1,1,3,3,3-hexamethyldisilazane and potassium 1,1,1,3,3,3-hexamethyldisilazane.

Examples of the halogenating agents include iodine, N-iodosuccinimide, bromine, N-bromosuccinimide, carbon tetrabromide, 1,2-dibromoethane, 1,2-dibromo-1,1,2,2-tetrafluoroethane, chlorine, N-chlorosuccinimide, carbon tetrachloride, xenon difluoride, N-fluorobenzenesulfonimide and N-fluoro-N'-(chloromethyl)triethylenediamine bis(tetrafluoroborate).

[Chem. 10]

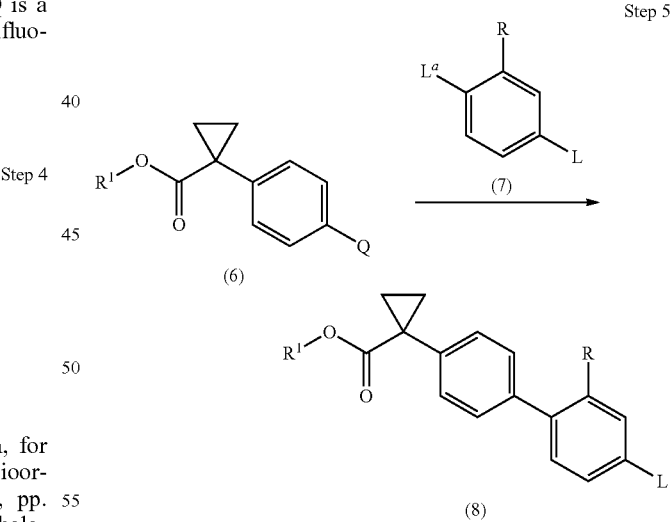

Step 5: In accordance with a method described in, for example, Tetrahedron, 58 (2002), pp. 9633-9695, Compound (6) and Compound (7) may be reacted in a reaction solvent in the presence of a coupling catalyst, a ligand, and/or a base to synthesize Compound (8).

Preferred examples of the reaction solvents include aliphatic hydrocarbons, aromatic hydrocarbons, ethers, ketones, esters, nitriles, alcohols, amides, sulfoxides, sulfones, water and a mixed solvent thereof. 1,4-Dioxane/water mixture is more preferable.

Examples of the coupling catalysts include palladium catalysts such as tetrakis(triphenylphosphine)palladium (0), [1,1'-bis(diphenylphosphino)ferrocene]palladium (II) dichloride methylene chloride adduct, bis(triphenylphosphine)palladium (II) dichloride, tris(dibenzylideneacetone)dipalladium (0) and palladium (II) acetate; and nickel catalysts such as bis(triphenylphosphine) nickel (II) dichloride.

Examples of the ligands, sometimes present in the coupling catalysts themselves, include triphenylphosphine, [1,1'-bis(diphenylphosphino)ferrocene], dibenzylideneacetone, triphenylarsine, tri(o-tolyl)phosphine, tri-tert-butylphosphine and tricyclohexylphosphine.

Examples of the bases include fluoride salts such as potassium fluoride and cesium fluoride; carbonate salts such as sodium hydrogencarbonate, sodium carbonate, potassium carbonate, cesium carbonate and thallium carbonate; metal hydroxides such as sodium hydroxide, potassium hydroxide, barium hydroxide and thallium hydroxide; phosphate salts such as potassium phosphate; and organic bases such as triethylamine and diisopropylethylamine. Sodium carbonate is preferable.

[Chem. 11]

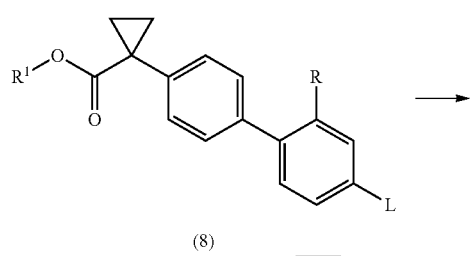

Step 6: In accordance with a method described in, for example, Journal of the American Chemical Society, 129 (2007), pp. 4595-4605, Compound (8) may be reacted in a reaction solvent in the presence of a palladium catalyst, a ligand, a boronic acid reagent, and/or a base to synthesize Compound (9). For example, L represents a chlorine atom, a bromine atom, an iodine atom, or a trifluoromethanesulfonyloxy group, and Q represents boronic acid or a boronate ester.

Preferred examples of the reaction solvents include aliphatic hydrocarbons, aromatic hydrocarbons, ethers, ketones, esters, nitriles, alcohols, amides, sulfoxides, sulfones, water and a mixed solvent thereof. 1,4-Dioxane is more preferable.

Examples of the palladium catalysts include tetrakis(triphenylphosphine)palladium (0), [1,1'-bis(diphenylphosphino)ferrocene]palladium (II) dichloride methylene chloride adduct, bis(triphenylphosphine)palladium (II) dichloride, tris(dibenzylideneacetone)dipalladium (0) and palladium (II) acetate. [1,1'-Bis(diphenylphosphino)ferrocene]palladium (II) dichloride methylene chloride adduct and palladium (II) acetate are preferable.

Examples of the ligands, sometimes present in the coupling catalysts themselves, include triphenylphosphine, [1,1'-bis(diphenylphosphino)ferrocene], dibenzylideneacetone, triphenylarsine, tri(o-tolyl)phosphine, tri-tert-butylphosphine and tricyclohexylphosphine. Tricyclohexylphosphine is preferable.

Examples of the boronic acid reagents include 4,4,4',4',5,5,5',5'-octamethyl-2,2'-bi(1,3,2-dioxaborolane) and 4,4,5,5-tetramethyl-1,3,2-dioxaborolane.

Examples of the bases include potassium acetate and sodium acetate.

Alternatively, in accordance with a method described in, for example, Angewandte Chemie—International Edition, 45 (2006), pp. 1404-1408, Compound (8) in which L is a chlorine atom, a bromine atom or an iodine atom may be treated in a reaction solvent so as to subject the halogen group L to halogen-metal exchange using a base, and subsequently the product may be treated with a boronic acid reagent to synthesize Compound (9).

Preferred examples of the reaction solvents include aliphatic hydrocarbons, aromatic hydrocarbons, halogenated hydrocarbons, ethers, amides, sulfoxides, sulfones and a mixed solvent thereof. Ethers, aliphatic hydrocarbons and a mixed solvent thereof are more preferable.

Examples of the bases include alkyllithiums such as n-butyllithium, sec-butyllithium and tert-butyllithium; and Grignard reagents such as ethylmagnesium bromide, ethylmagnesium chloride, isopropylmagnesium chloride and phenylmagnesium chloride.

Examples of the boronic acid reagents include trimethyl borate, triisopropyl borate, trihexadecyl borate and 2-isopropoxy-4,4,5,5-tetramethyl-1,3,2-dioxaborolane.

[Chem. 12]

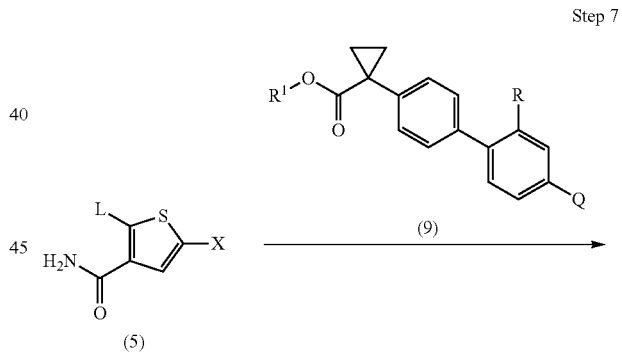

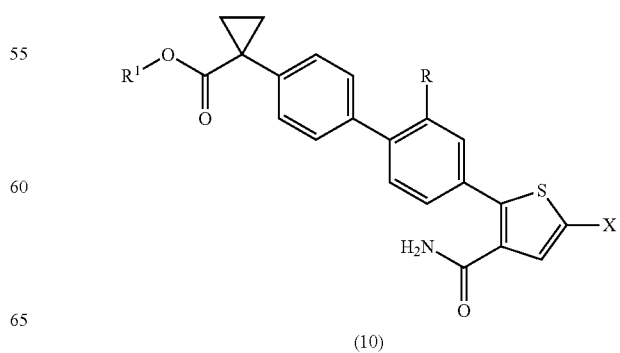

-continued

[Chem. 13]

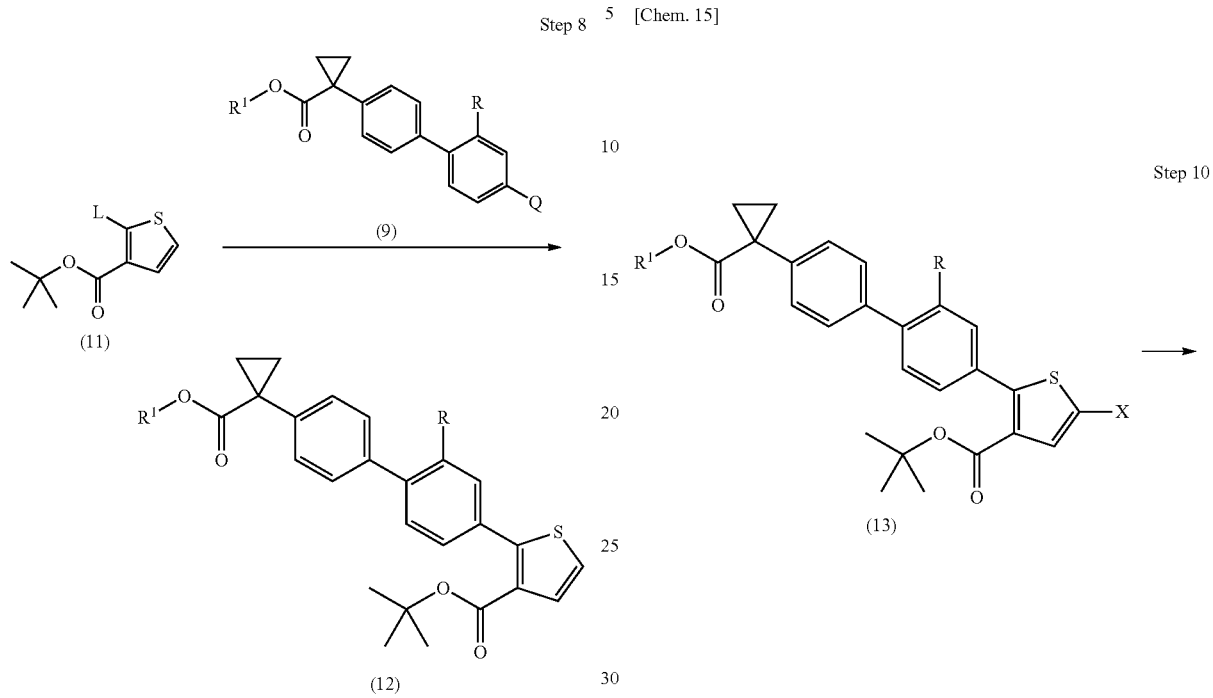

Step 7 and Step 8: Compound (5) or Compound (11) and Compound (9) may be reacted in the similar manner to Step 5 to synthesize Compound (10) or Compound (12), respectively.

[Chem. 14]

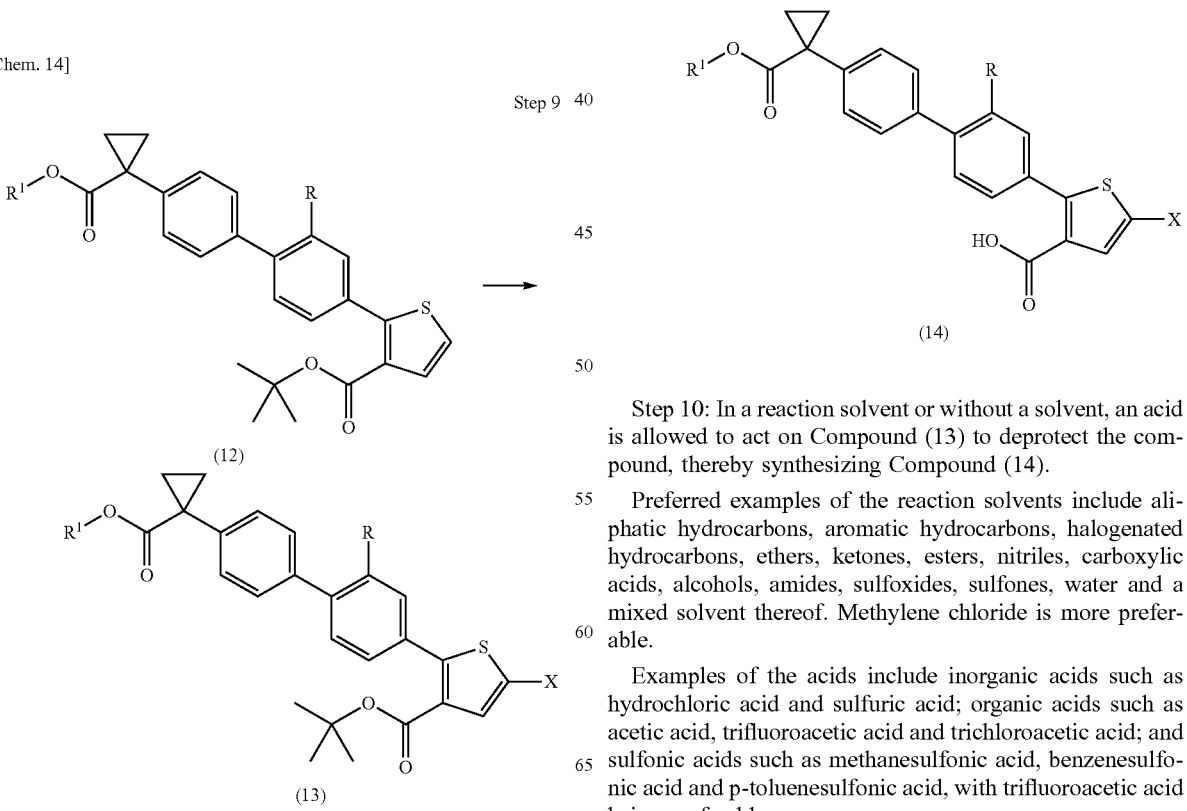

Step 9: Compound (12) may be treated in the similar manner to Step 4 to synthesize Compound (13).

[Chem. 15]

Step 10: In a reaction solvent or without a solvent, an acid is allowed to act on Compound (13) to deprotect the compound, thereby synthesizing Compound (14).

Preferred examples of the reaction solvents include aliphatic hydrocarbons, aromatic hydrocarbons, halogenated hydrocarbons, ethers, ketones, esters, nitriles, carboxylic acids, alcohols, amides, sulfoxides, sulfones, water and a mixed solvent thereof. Methylene chloride is more preferable.

Examples of the acids include inorganic acids such as hydrochloric acid and sulfuric acid; organic acids such as acetic acid, trifluoroacetic acid and trichloroacetic acid; and sulfonic acids such as methanesulfonic acid, benzenesulfonic acid and p-toluenesulfonic acid, with trifluoroacetic acid being preferable.

[Chem. 16]

[Chem. 17]

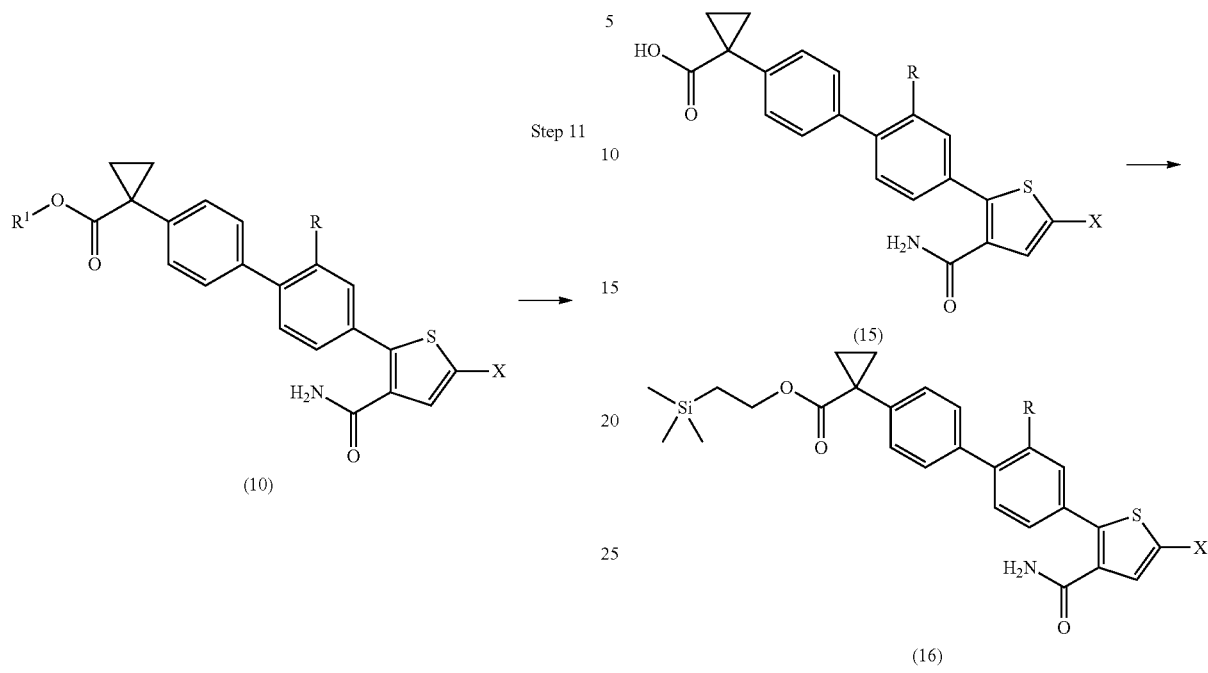

Step 11: In a reaction solvent, Compound (10) is hydrolyzed in the presence of an acid or a base to synthesize Compound (15).

Preferred examples of the reaction solvents include aliphatic hydrocarbons, aromatic hydrocarbons, halogenated hydrocarbons, ethers, ketones, nitriles, carboxylic acids, alcohols, amides, sulfoxides, sulfones, water and a mixed solvent thereof. Ethanol/tetrahydrofuran/water mixture and 2-propanol/tetrahydrofuran/water mixture are more preferable.

Examples of the acids and the bases include inorganic acids such as hydrochloric acid and sulfuric acid; organic acids such as acetic acid and trifluoroacetic acid; sulfonic acids such as methanesulfonic acid, benzenesulfonic acid and p-toluenesulfonic acid; alkali metal hydroxides such as lithium hydroxide, sodium hydroxide and potassium hydroxide; and alkali metal carbonate salts such as potassium carbonate and sodium carbonate. The use of a base is preferable, and the use of lithium hydroxide or sodium hydroxide is more preferable.

Step 12: In a reaction solvent, Compound (15) may be condensed with trimethylsilylethanol using a condensing agent in the presence or absence of a base and in the presence or absence of an additive, thereby synthesizing Compound (16).

Preferred examples of the reaction solvents include aliphatic hydrocarbons, aromatic hydrocarbons, halogenated hydrocarbons, ethers, ketones, esters, nitriles, amides, sulfoxides, sulfones and a mixed solvent thereof. N,N-dimethylformamide is more preferable.

Examples of the bases include carbonate salts such as sodium hydrogencarbonate, sodium carbonate, potassium carbonate, cesium carbonate and thallium carbonate; pyridines such as pyridine, 2,6-lutidine and 4-picoline; and organic bases such as triethylamine and diisopropylethylamine. Diisopropylethylamine is preferable.

Examples of the condensing agents include carbodiimide condensing agents such as N,N'-dicyclohexylcarbodiimide, N,N'-diisopropylcarbodiimide, 1-ethyl-3-(3-dimethylaminopropyl)carbodiimide hydrochloride and N-cyclohexyl-N'-(2-morpholinoethyl)carbodiimide metho-p-toluenesulfonate salt; imidazole condensing agents such as N,N'-carbonyldiimidazole; triazine condensing agents such as 4-(4,6-dimethoxy-1,3,5-triazin-2-yl)-4-methylmorpholinium chloride and (4,6-dimethoxy-1,3,5-triazin-2-yl)-(2-octoxy-2-oxoethyl)dimethylammonium trifluoromethanesulfonate; phosphonium condensing agents such as 1H-benzotriazol-1-yloxytris(dimethylamino)phosphonium hexafluorophosphate salt, 1H-benzotriazol-1-yloxytripyrrolidinophosphonium hexafluorophosphate salt and chlorotripyrrolidinophosphonium hexafluorophosphate salt; and uronium condensing agents such as ({[(1-cyano-2-ethoxy-2-oxoethylidene)amino]oxy}-4-morpholinomethylene)dimethylammonium hexafluorophosphate salt, O-(benzotriazol-1-yl)-N,N,N',N'-tetramethyluronium hexafluorophosphate salt, O-(7-azabenzotriazol-1-yl)-N,N,N',N'-tetramethyluronium hexafluorophosphate salt, O-(N-succinimidyl)-N,N,N', N'-tetramethyluronium tetrafluoroborate salt and O-(3,4-dihydro-4-oxo-1,2,3-benzotriazin-3-yl)-N,N-N',N'-tetramethyluronium tetrafluoroborate salt, with O-(benzotriazol-1-yl)-N,N,N',N'-tetramethyluronium hexafluorophosphate salt being preferable.

Examples of the additives include benzotriazoles such as 1-hydroxybenzotriazole and 1-hydroxyazabenzotriazole; pyridines such as N,N-dimethylaminopyridine; and combinations thereof. N,N-dimethylaminopyridine is preferable.

[Chem. 18]

Step 13

(17) → (18)

Step 13: In accordance with a method described in, for example, Tetrahedron Letters, 47 (2006), pp. 5261-5264, Compound (17) may be reduced with a reducing agent in a reaction solvent to synthesize Compound (18).

Preferred examples of the reaction solvents include aliphatic hydrocarbons, aromatic hydrocarbons, halogenated hydrocarbons, ethers, esters, nitriles, alcohols, amides, sulfoxides, sulfones, water and a mixed solvent thereof.

Examples of the reducing agents include borohydrides such as lithium borohydride, sodium borohydride, potassium borohydride and sodium trimethoxyborohydride; and aluminum hydrides such as lithium aluminum hydride, sodium aluminum hydride, diisobutylaluminum hydride and lithium trimethoxyaluminum hydride.

Optically active Compound (18) may be synthesized by using (R)- or (S)-5,5-diphenyl-2-methyl-3,4-propano-1,3,2-oxazaborolidine, etc. in accordance with a method described in, for example, Journal of Organic Chemistry, 56 (1991), pp. 763-769.

The optical purity of Compound (18) obtained by the above method may be increased by a known method such as using an enzyme or a resolving agent or by a combination of such methods.

[Chem. 19]

Step 14

(10) + (18) →

(3)

[Chem. 20]

Step 15

(16) + (18) →

(19)

Step 14 and Step 15: In a reaction solvent or without a solvent, Compound (10) or Compound (16) is subjected to Hofmann rearrangement in the presence or absence of a base using Compound (18) and an oxidizing agent in accordance with a method described in, for example, Organic Synthesis, 66 (1988), pp. 132-137, thereby synthesizing Compound (3) or Compound (19), respectively.

Preferred examples of the reaction solvents include aliphatic hydrocarbons, aromatic hydrocarbons, halogenated hydrocarbons, ethers, ketones, esters, nitriles, amides, sulfoxides, sulfones and a mixed solvent thereof. Toluene is more preferable.

Examples of the bases include organic amines such as triethylamine and diisopropylethylamine; and pyridines such as pyridine, 2,6-lutidine and 4-picoline. Pyridine is preferable.

Examples of the oxidizing agents include high-valence iodine compounds such as [bis(acetoxy)iodo]benzene, [bis(trifluoroacetoxy)iodo]benzene and iodosylbenzene, with [bis(trifluoroacetoxy)iodo]benzene being preferable.

[Chem. 21]

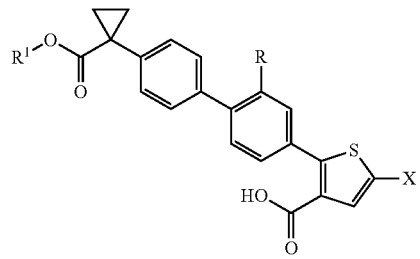

(14)

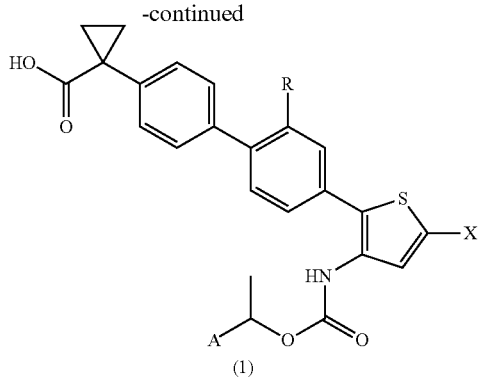

(5)

Step 17: Compound (3) may be treated in the similar manner to Step 11 to synthesize Compound (1).

[Chem. 23]

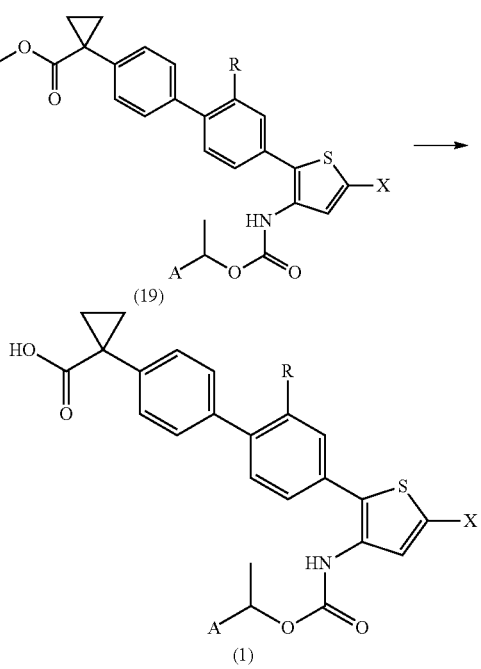

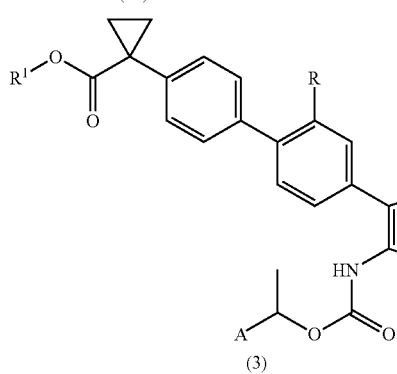

(3)

Step 16: In a reaction solvent or without a solvent, Compound (14) may be subjected to Curtius rearrangement using Compound (18), diphenylphosphoryl azide and a base in accordance with a method described in, for example, Journal of the American Chemical Society, 94 (1972), pp. 6203-6205, thereby synthesizing Compound (3).

Preferred examples of the reaction solvents include aliphatic hydrocarbons, aromatic hydrocarbons, halogenated hydrocarbons, ethers, ketones, esters, nitriles, amides, sulfoxides, sulfones, water and a mixed solvent thereof. Toluene is more preferable.

Examples of the bases include organic amines such as triethylamine and diisopropylethylamine, with triethylamine being preferable.

[Chem. 22]

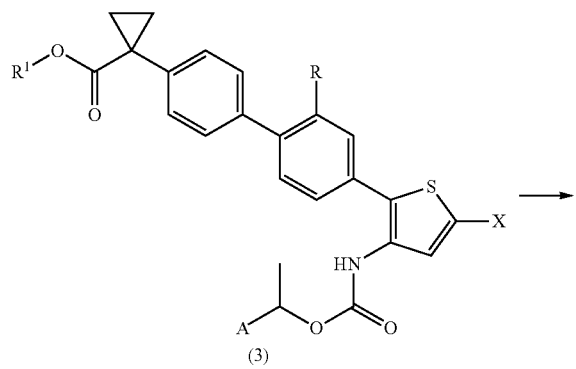

(3)

Step 18: In a reaction solvent, Compound (19) may be deprotected with a deprotecting reagent to synthesize Compound (1).

Preferred examples of the reaction solvents include aliphatic hydrocarbons, aromatic hydrocarbons, halogenated hydrocarbons, ethers, ketones, esters, nitriles, carboxylic acids, alcohols, amides, sulfoxides, sulfones, water and a mixed solvent thereof. N,N-dimethylformamide is more preferable.

Examples of the deprotecting reagents include hydrofluoric acid; inorganic fluoride salts such as potassium fluoride; organic hydrofluoride salts such as pyridine hydrofluoride salt, triethylamine hydrofluoride salt and 1-hexadecane hydrofluoride salt; ammonium fluorides such as tetraethylammonium fluoride and tetrabutylammonium fluoride; and difluorotrimethylsilicate salts such as tris(dimethylamino) sulfonium difluorotrimethylsilicate. Tetrabutylammonium fluoride is preferable.

Compound of the formula (I') may be synthesized by treating Compound of the formula (1) in accordance with Step 1 using $M^{m'+}(OH^-)_{n'}$.

The target compound produced in each reaction may be recovered from the reaction mixture liquid by a common method. In the case where, for example, the target compound is completely or partly precipitated, deposited or crystallized in the reaction mixture liquid, the solid containing the target compound may be obtained by filtering the reaction mixture liquid. When the target compound is completely or partly dissolved in the reaction mixture liquid, the target compound may be obtained by removing the solvent (for example, by freeze drying) directly or after insoluble matters are removed by filtration. Alternatively, the target compound may be obtained by appropriately neutralizing the reaction mixture liquid, removing any insoluble matters by filtration, adding a water-immiscible organic solvent such as ethyl acetate, washing the mixture liquid with water, separating the organic phase containing the target compound, drying the organic phase with a desiccant such as anhydrous magnesium sulfate or anhydrous sodium sulfate, and evaporating the solvent by distillation.

Where necessary, the target compound obtained may be separated and purified by an appropriate combination of common methods such as washing with water, an organic solvent or a mixture of such solvents; recrystallization; reprecipitation; and methods commonly used for the separation and purification of organic compounds (for example, adsorption column chromatography methods using a carrier such as silica gel or alumina; ion exchange chromatography methods; normal-phase or reverse-phase column chromatography (preferably, high-performance liquid chromatography) methods using silica gel or alkylated silica gel; and normal-phase or reverse-phase column chromatography (preferably, high-performance liquid chromatography) methods using a filler in which optically active molecules are fixed or in which silica gel is coated with optically active molecules).

When the salts of the present invention represented by the general formula (I) are used as medicaments, the salts themselves (as an ingredient) may be administered as such or may be administered orally or parenterally (such as by intravenous administration, intramuscular administration, intraperitoneal administration, percutaneous administration, intratracheal administration, intracutaneous administration or subcutaneous administration) in forms such as tablets, capsules, powders, syrups, granules, fine granules, pills, suspensions, emulsions, percutaneous absorption preparations, suppositories, ointments, lotions, inhalants and injection products, which are manufactured by mixing the salts with appropriate pharmacologically acceptable excipients, diluents, etc.

These preparations are manufactured by known methods using additives such as excipients, lubricants, binders, disintegrants, emulsifiers, stabilizers, flavoring agents and diluents.

Examples of the excipients include organic excipients and inorganic excipients. Examples of the organic excipients include sugar derivatives such as lactose, sucrose, glucose, mannitol and sorbitol; starch derivatives such as corn starch, potato starch, α-starch and dextrin; cellulose derivatives such as crystalline cellulose; gum arabic; dextran; and pullulan. Examples of the inorganic excipients include light anhydrous silicic acid; and sulfate salts such as calcium sulfate.

Examples of the lubricants include stearic acid; a metal salt of stearic acid such as calcium stearate and magnesium stearate; talc; colloidal silica; waxes such as bees wax and spermaceti wax; boric acid; adipic acid; sulfate salts such as sodium sulfate; glycol; fumaric acid; sodium benzoate; D,L-leucine; sodium laurylsulfate; silicic acids such as silicic anhydride and silicic acid hydrate; and starch derivatives listed as the excipients above.

Examples of the binders include hydroxypropylcellulose, hydroxypropylmethylcellulose, polyvinylpyrrolidone, macrogol and compounds listed as the excipients above.

Examples of the disintegrants include cellulose derivatives such as low-substituted hydroxypropylcellulose, carboxymethylcellulose, carboxymethylcellulose calcium and internally-crosslinked carboxymethylcellulose calcium; crosslinked polyvinylpyrrolidone; and chemically modified starch or cellulose derivatives such as carboxymethyl starch and sodium carboxymethyl starch.

Examples of the emulsifiers include colloidal clays such as bentonite and bee gum; anionic surfactants such as sodium laurylsulfate; cationic surfactants such as benzalkonium chloride; and nonionic surfactants such as polyoxyethylene alkyl ether, polyoxyethylene sorbitan fatty acid ester and sucrose fatty acid ester.

Examples of the stabilizers include p-hydroxybenzoate esters such as methylparaben and propylparaben; alcohols such as chlorobutanol, benzyl alcohol and phenylethyl alcohol; benzalkonium chloride; phenols such as phenol and cresol; thimerosal; acetic anhydride; and sorbic acid.

Examples of the flavoring agents include sweeteners such as saccharin sodium and aspartame; acidulants such as citric acid, malic acid and tartaric acid; and flavors such as menthol, lemon extract and orange extract.

The diluents are compounds usually used for dilution. Examples thereof include lactose, mannitol, glucose, sucrose, calcium sulfate, hydroxypropylcellulose, microcrystalline cellulose, water, ethanol, polyethylene glycol, propylene glycol, glycerol, starch, polyvinylpyrrolidone and mixtures thereof.

The dose of the salts of the present invention represented by the general formula (I) may vary depending on conditions such as symptoms, ages and body weights of patients. In the case of oral administration, the lower and upper limit doses per administration may be 0.001 mg/kg (preferably 0.01 mg/kg) and 20 mg/kg (preferably 10 mg/kg), respectively. In the case of parenteral administration, the lower and upper limit doses per administration may be 0.0001 mg/kg (preferably 0.0005 mg/kg) and 10 mg/kg (preferably 5 mg/kg), respectively. In both cases, the number of administrations for adults may be 1 to 6 per day depending on symptoms.

EXAMPLES

The present invention will be described in further detail hereinbelow by presenting Examples (Examples 1 to 15), Reference Examples (Reference Examples 1 to 32), Test Examples (Test Examples 1 to 8), and Preparation Examples (1 to 3). These examples only serve to help the understanding of the present invention and do not intend to limit the scope of the present invention.

Of the properties in Examples and Reference Examples, the Rf values are values measured with a thin layer chromatograph (Merck Co., TLC plate silica gel 60F$_{254}$ (trade name)). Developing solvents (and their volume ratio) are described in parentheses.

The term COOH column in silica gel column chromatography indicates Chromatorex (registered trademark) Q-PACK COOH silica gel prepacked column by Fuji Silysia Chemical Ltd.

Ultrapure water by Wako Pure Chemical Industries, Ltd. (214-01301) was used.

In the case where a plurality of mass spectral values were obtained due to the presence of isotopes, only the smallest m/z value was described. DUIS in mass spectroscopy is a mixed ionization mode of ESI and APCI.

In the chemical structures, Me indicates a methyl group unless otherwise specified.

Example 1

Sodium (R)-1-[4'-(5-chloro-3-{[(1-phenylethoxy)carbonyl]amino}thiophen-2-yl)-2'-methoxy-[1,1'-biphenyl]-4-yl]cyclopropanecarboxylate (Compound No. I-2)

[Chem. 24]

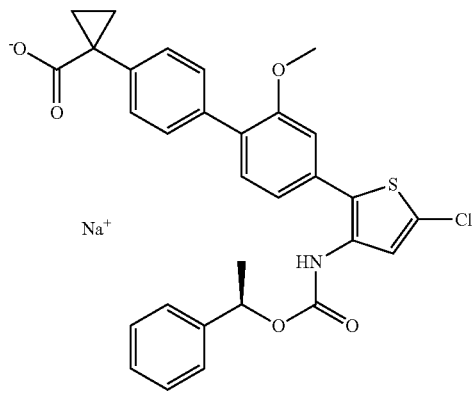

In an ice bath and while performing stirring, 2.00 ml (2.00 mmol) of a 1N aqueous sodium hydroxide solution was added to an acetonitrile (80 ml) suspension of 1.10 g (2.00 mmol) of (R)-1-[4'-(5-chloro-3-{[(1-phenylethoxy)carbonyl]amino}thiophen-2-yl)-2'-methoxy-[1,1'-biphenyl]-4-yl]cyclopropanecarboxylic acid synthesized in analogy to Reference Example 29. Thereafter, ultrapure water (6 ml) was added and the mixture was ultrasonicated to give a uniform solution, which was then stirred at room temperature for 3 hours. A small amount of ultrapure water was further added to the reaction mixture liquid. The solvent was removed by freeze drying, and the residue was dried by vacuum heating to give the title compound weighing 1.08 g (1.89 mmol, yield 95%) as a white solid.

Mass spectrum (ESI$^+$, m/z): 570 [M+1]$^+$.

$^1$H-NMR spectrum (400 MHz, DMSO-d$_6$) δ: 9.44 (1H, brs), 7.43-7.22 (10H, m), 7.21-7.14 (2H, m), 7.08 (1H, dd, J=7.8, 1.4 Hz), 5.75 (1H, q, J=6.1 Hz), 3.73 (3H, s), 1.56-1.38 (3H, m), 1.16 (2H, dd, J=5.6, 2.6 Hz), 0.66 (2H, dd, J=5.7, 2.7 Hz).

Example 2

Potassium (R)-1-[4'-(5-chloro-3-{[(1-phenylethoxy)carbonyl]amino}thiophen-2-yl)-2'-methoxy-[1,1'-biphenyl]-4-yl]cyclopropanecarboxylate (Compound No. I-4)

[Chem. 25]

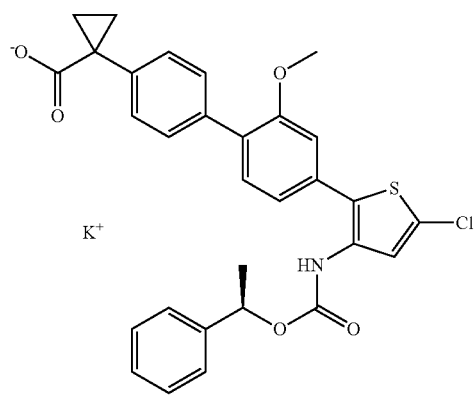

While performing stirring, 0.500 ml (0.500 mmol) of a 1N aqueous potassium hydroxide solution was added to an acetonitrile (20 ml)-ultrapure water (1.5 ml) suspension of 275 mg (0.501 mmol) of (R)-1-[4'-(5-chloro-3-{[(1-phenylethoxy)carbonyl]amino}thiophen-2-yl)-2'-methoxy-[1,1'-biphenyl]-4-yl]cyclopropanecarboxylic acid synthesized in analogy to Reference Example 29, thereby preparing a uniform solution. Thereafter, ultrapure water (6 ml) was added and the mixture was ultrasonicated. The resultant reaction mixture liquid was allowed to stand at room temperature for 30 minutes. A small amount of ultrapure water was further added. The solvent was removed by freeze drying, and the residue was dried by vacuum heating to give the title compound weighing 235 mg (0.401 mmol, yield 80%) as a white solid.

Mass spectrum (ESI$^+$, m/z): 586 [M+1]$^+$.

$^1$H-NMR spectrum (400 MHz, DMSO-d$_6$) δ: 9.44 (1H, brs), 7.43-7.14 (12H, m), 7.08 (1H, dd, J=7.8, 1.4 Hz), 5.75 (1H, q, J=6.2 Hz), 3.73 (3H, s), 1.54-1.39 (3H, m), 1.11 (2H, dd, J=5.8, 2.7 Hz), 0.60 (2H, dd, J=5.8, 2.6 Hz).

Example 3

½ Calcium (R)-1-[4'-(5-chloro-3-{[(1-phenylethoxy)carbonyl]amino}thiophen-2-yl)-2'-methoxy-[1,1'-biphenyl]-4-yl]cyclopropanecarboxylate (Compound No. I-6)

[Chem. 26]

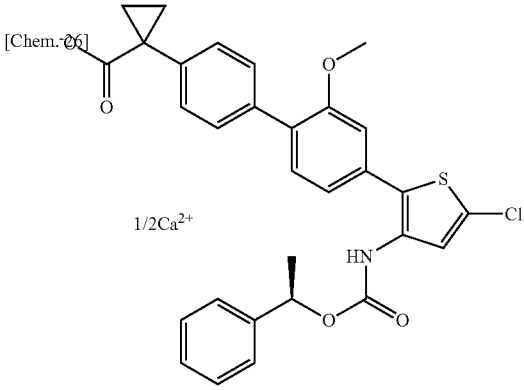

0.180 ml (0.090 mmol) of a 0.5 M aqueous calcium acetate solution was added to an ultrapure water (25 ml) solution of 101 mg (0.177 mmol) of sodium (R)-1-[4'-(5-chloro-3-{[(1-phenylethoxy)carbonyl]amino}thiophen-2-yl)-2'-methoxy-[1,1'-biphenyl]-4-yl]cyclopropanecarboxylate obtained in Example 1. The mixture was stirred at room temperature for 2 days. The resultant suspension was filtered through a membrane filter (Millipore). The residue was washed with ultrapure water and was dried by vacuum heating to give the title compound weighing 40.4 mg (0.071 mmol, yield 40%) as a white solid.

Mass spectrum (ESI$^+$, m/z): 1133 [2M+1]$^+$.

$^1$H-NMR spectrum (400 MHz, DMSO-d$_6$) δ: 9.42 (1H, brs), 7.41-7.25 (10H, m), 7.19-7.15 (2H, m), 7.07 (1H, dd, J=7.9, 1.3 Hz), 5.75 (1H, q, J=6.2 Hz), 3.72 (3H, s), 1.54-1.38 (3H, m), 1.38-1.22 (2H, m), 0.90-0.80 (2H, m).

Example 4

Sodium (R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylate (Compound No. I-8)

[Chem. 27]

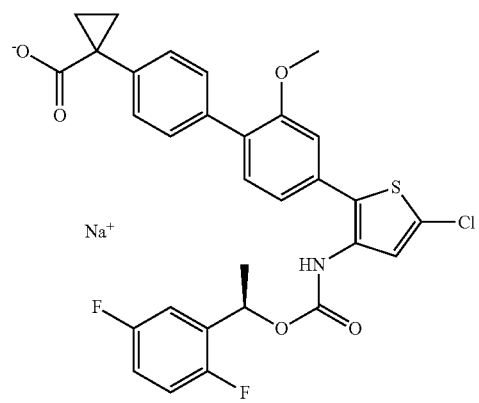

In an ice bath and while performing stirring, 1.00 ml (1.00 mmol) of a 1N aqueous sodium hydroxide solution was added to an acetonitrile (40 ml)-ultrapure water (3 ml) suspension of 584 mg (1.00 mmol) of (R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylic acid synthesized in analogy to Reference Example 32, thereby preparing a uniform solution. The solution was stirred at the temperature for 30 minutes. A small amount of ultrapure water was further added to the reaction mixture liquid. The solvent was removed by freeze drying, and the residue was dried by vacuum heating to give the title compound weighing 534 mg (0.882 mmol, yield 88%) as a white solid.

Mass spectrum (ESI$^+$, m/z): 606 [M+1]$^+$.

$^1$H-NMR spectrum (400 MHz, DMSO-d$_6$) δ: 9.56 (1H, brs), 7.36-7.14 (10H, m), 7.08 (1H, dd, J=7.8, 1.4 Hz), 5.91 (1H, q, J=6.6 Hz), 3.75 (3H, s), 1.61-1.36 (3H, m), 1.16 (2H, dd, J=5.6, 2.8 Hz), 0.66 (2H, dd, J=5.6, 2.6 Hz).

Example 5

Potassium (R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylate (Compound No. I-10)

[Chem. 28]

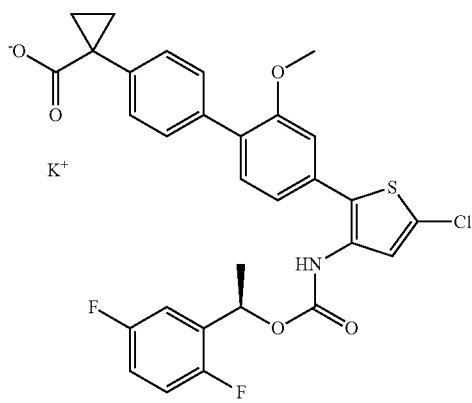

In an ice bath and while performing stirring, 0.500 ml (0.500 mmol) of a 1N aqueous potassium hydroxide solution was added to an acetonitrile (20 ml)-ultrapure water (1.5 ml) uniform solution of 292 mg (0.500 mmol) of (R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylic acid synthesized in analogy to Reference Example 32. The mixture was stirred at the temperature for 1 hour. A small amount of ultrapure water was further added to the reaction mixture liquid. The solvent was removed by freeze drying, and the residue was dried by vacuum heating to give the title compound weighing 276 mg (0.444 mmol, yield 89%) as a white solid.

Mass spectrum (ESI$^+$, m/z): 622 [M+1]$^+$.

$^1$H-NMR spectrum (400 MHz, DMSO-d$_6$) δ: 9.56 (1H, brs), 7.33-7.14 (10H, m), 7.08 (1H, dd, J=7.8, 1.1 Hz), 5.91 (1H, q, J=6.1 Hz), 3.75 (3H, s), 1.58-1.40 (3H, m), 1.12 (2H, dd, J=5.7, 2.7 Hz), 0.61 (2H, dd, J=5.6, 2.5 Hz).

Example 6

½ Calcium (R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylate (Compound No. I-12)

[Chem. 29]

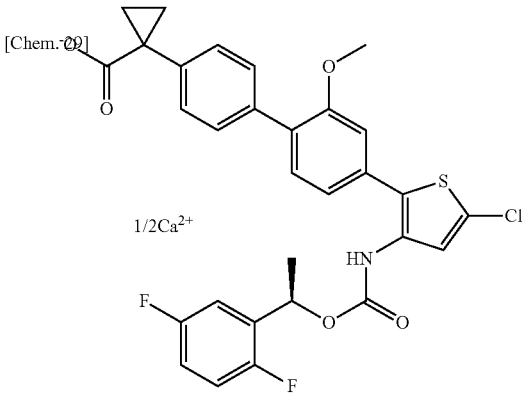

acetate solution was added to an ultrapure water (25 ml) uniform solution of 100 mg (0.165 mmol) of sodium (R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylate obtained in Example 4. The mixture was stirred at room temperature for 2 days. The resultant suspension was filtered through a membrane filter (Millipore). The residue was washed with ultrapure water and was dried by vacuum heating to give the title compound weighing 47.8 mg (0.079 mmol, yield 48%) as a light yellow solid.

Mass spectrum (ESI$^+$, m/z): 1205 [2M+1]$^+$.

$^1$H-NMR spectrum (400 MHz, DMSO-d$_6$) δ: 9.55 (1H, brs), 7.38-7.14 (10H, m), 7.07 (1H, dd, J=7.8, 1.6 Hz), 5.90 (1H, q, J=6.4 Hz), 3.75 (3H, s), 1.60-1.40 (3H, m), 1.40-1.20 (2H, m), 0.91-0.78 (2H, m).

Example 7

Sodium (R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylate (Compound No. I-14)

[Chem. 30]

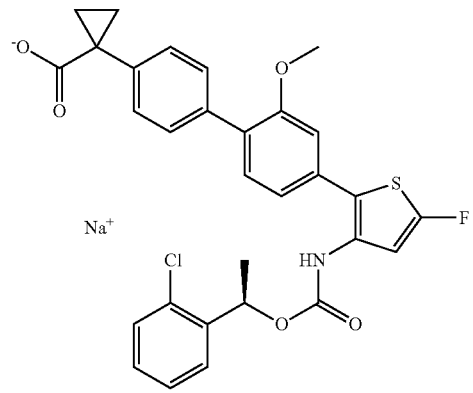

In an ice bath and while performing stirring, 2.00 ml (2.00 mmol) of a 1N aqueous sodium hydroxide solution was added to an acetonitrile (80 ml)-ultrapure water (6 ml) suspension of 1.13 g (2.00 mmol) of (R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylic acid synthesized in analogy to Reference Example 31. The mixture was ultrasonicated to give a uniform solution, which was then allowed to stand at the temperature for 3 hours. A small amount of ultrapure water was further added to the reaction mixture liquid. The solvent was removed by freeze drying, and the residue was dried by vacuum heating to give the title compound weighing 1.15 g (1.96 mmol, yield 98%) as a white solid.

Mass spectrum (ESI$^+$, m/z): 588 [M+1]$^+$.

1H-NMR spectrum (400 MHz, DMSO-d$_6$) δ: 9.55 (1H, brs), 7.62-7.22 (9H, m), 7.14-7.20 (1H, m), 7.07 (1H, dd, J=7.8, 1.2 Hz), 6.84 (1H, d, J=2.5 Hz), 6.00 (1H, q, J=5.6 Hz), 3.76 (3H, s), 1.59-1.35 (3H, m), 1.16 (2H, dd, J=5.7, 2.7 Hz), 0.66 (2H, dd, J=5.6, 2.6 Hz)

Example 8

Potassium (R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylate (Compound No. I-16)

[Chem. 31]

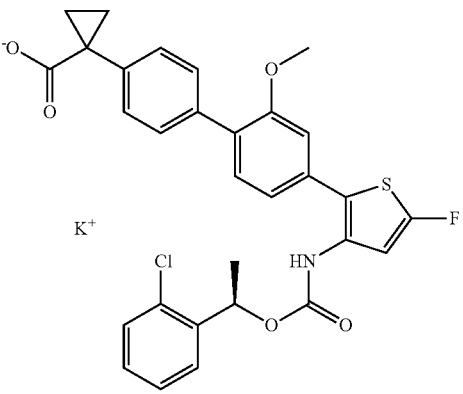

At room temperature, 0.500 ml (0.500 mmol) of a 1N aqueous potassium hydroxide solution was added to an acetonitrile (20 ml)-ultrapure water (1.5 ml) suspension of 284 mg (0.501 mmol) of (R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylic acid synthesized in analogy to Reference Example 31. The mixture was ultrasonicated to give a uniform solution, which was then allowed to stand at room temperature for 1 hour. A small amount of ultrapure water was further added to the reaction mixture liquid. The solvent was removed by freeze drying, and the residue was dried by vacuum heating to give the title compound weighing 270 mg (0.447 mmol, yield 89%) as a white solid.

Mass spectrum (ESI$^+$, m/z): 604 [M+1]$^+$.

$^1$H-NMR spectrum (400 MHz, DMSO-d$_6$) δ: 9.56 (1H, brs), 7.60-7.21 (9H, m), 7.19-7.14 (1H, m), 7.07 (1H, dd, J=7.9, 1.4 Hz), 6.84 (1H, d, J=2.4 Hz), 6.00 (1H, q, J=6.4 Hz), 3.76 (3H, s), 1.55-1.37 (3H, m), 1.12 (2H, dd, J=5.8, 2.7 Hz), 0.61 (2H, dd, J=5.8, 2.6 Hz).

Example 9

½ Calcium (R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylate (Compound No. I-18)

[Chem. 32]

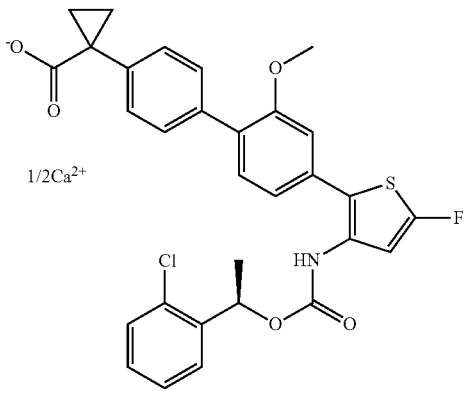

At room temperature and while performing stirring, 0.500 ml (0.500 mmol) of a 1N aqueous sodium hydroxide solution was added to an acetonitrile (20 ml)-ultrapure water (1.5 ml) suspension of 282 mg (0.498 mmol) of (R)-1-{4'-[3-({[1-(2-chlorophenyl)ethoxy]carbonyl}amino)-5-fluoro-thiophen-2-yl]-2'-methoxy-[1,1'-biphenyl]-4-yl}cyclopropanecarboxylic acid synthesized in analogy to Reference Example 31. The mixture was ultrasonicated to give a uniform solution. Next, 0.500 ml (0.085 mmol) of a 0.5 M aqueous calcium acetate solution was added to the reaction mixture liquid and stirring was performed at room temperature for 1 hour. Acetonitrile was distilled off from the reaction mixture liquid, and ultrapure water was added. The resultant mixture was stirred at room temperature for 18 hours. The resultant suspension was filtered, and the residue was washed with ultrapure water and was dried by vacuum heating to give the title compound weighing 213 mg (0.365 mmol, yield 73%) as a white solid.

Mass spectrum (ESI$^+$, m/z): 1169 [2M+1]$^+$.

$^1$H-NMR spectrum (400 MHz, DMSO-$d_6$) δ: 9.54 (1H, brs), 7.58-7.25 (9H, m), 7.17 (1H, d, J=1.3 Hz), 7.07 (1H, dd, J=7.8, 1.1 Hz), 6.84 (1H, d, J=2.5 Hz), 6.00 (1H, q, J=6.5 Hz), 3.75 (3H, s), 1.57-1.38 (3H, m), 1.38-1.18 (2H, m), 0.90-0.79 (2H, m).

Example 10

Sodium (R)-1-{4'-[5-chloro-3-({[1-(thiophen-3-yl)ethoxy]carbonyl}amino)thiophen-2-yl]-[1,1'-biphenyl]-4-yl}cyclopropanecarboxylate (Compound No. I-20)

[Chem. 33]

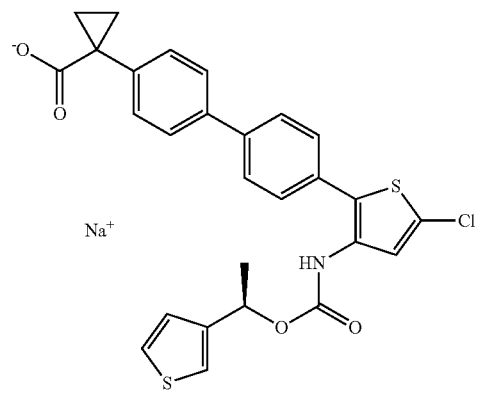

At room temperature and while performing stirring, 2.00 ml (2.00 mmol) of a 1N aqueous sodium hydroxide solution was added to an acetonitrile (80 ml) uniform solution of 1.05 g (2.00 mmol) of (R)-1-{4'-[5-chloro-3-({[1-(thiophen-3-yl)ethoxy]carbonyl}amino)thiophen-2-yl]-[1,1'-biphenyl]-4-yl}cyclopropanecarboxylic acid synthesized in analogy to Reference Example 28. The mixture was ultrasonicated and was stirred at the temperature for 4 hours. The resultant suspension was filtered, and the residue was washed with the mother liquor and was dried by vacuum heating to give the title compound weighing 1.06 g (1.94 mmol, yield 97%) as a white solid.

Mass spectrum (ESI$^+$, m/z): 546 [M+1]$^+$.

$^1$H-NMR spectrum (400 MHz, DMSO-$d_6$) δ: 9.34 (1H, brs), 7.70-7.65 (2H, m), 7.57-7.40 (6H, m), 7.35-7.30 (2H, m), 7.23-7.16 (1H, m), 7.16-7.08 (1H, m), 5.82 (1H, q, J=6.4 Hz), 1.61-1.40 (3H, m), 1.18 (2H, dd, J=5.8, 2.8 Hz), 0.68 (2H, dd, J=5.7, 2.7 Hz).

Example 11

Potassium (R)-1-{4'-[5-chloro-3-({[1-(thiophen-3-yl)ethoxy]carbonyl}amino)thiophen-2-yl]-[1,1'-biphenyl]-4-yl}cyclopropanecarboxylate (Compound No. I-22)

[Chem. 34]

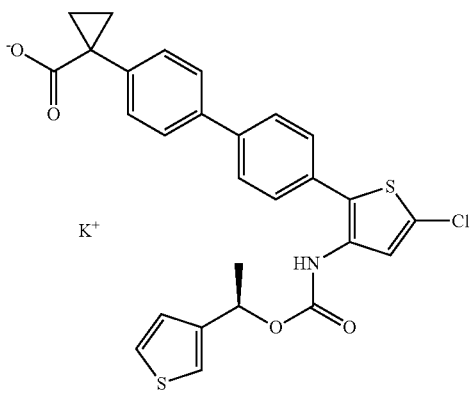

At room temperature and while performing stirring, 0.500 ml (0.500 mmol) of a 1N aqueous potassium hydroxide solution was added to an acetonitrile (20 ml) uniform solution of 262 mg (0.500 mmol) of (R)-1-{4'-[5-chloro-3-({[1-(thiophen-3-yl)ethoxy]carbonyl}amino)thiophen-2-yl]-[1,1'-biphenyl]-4-yl}cyclopropanecarboxylic acid synthesized in analogy to Reference Example 28. The mixture was ultrasonicated and was stirred at room temperature for 3.5 hours. The resultant suspension was filtered through a membrane filter (Millipore). The residue was washed with the mother liquor and was dried by vacuum heating to give the title compound weighing 220 mg (0.392 mmol, yield 78%) as a white solid.

Mass spectrum (ESI$^+$, m/z): 562 [M+1]$^+$.

$^1$H-NMR spectrum (400 MHz, DMSO-$d_6$) δ: 9.34 (1H, brs), 7.71-7.64 (2H, m), 7.58-7.39 (6H, m), 7.33-7.27 (2H, m), 7.24-7.16 (1H, m), 7.16-7.07 (1H, m), 5.82 (1H, q, J=6.5 Hz), 1.61-1.41 (3H, m), 1.13 (2H, dd, J=5.8, 2.7 Hz), 0.62 (2H, dd, J=5.8, 2.7 Hz).

Example 12

½Calcium (R)-1-{4'-[5-chloro-3-({[1-(thiophen-3-yl)ethoxy]carbonyl}amino)thiophen-2-yl]-[1,1'-biphenyl]-4-yl}cyclopropanecarboxylate (Compound No. I-24)

[Chem. 35]

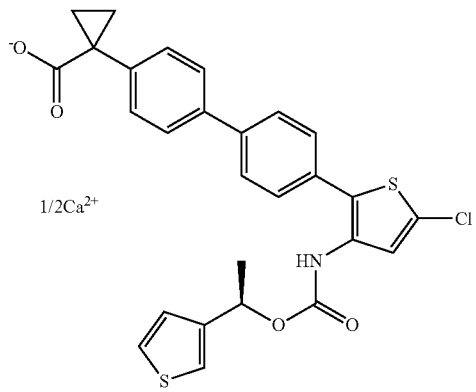

0.190 ml (0.095 mmol) of a 0.5 M aqueous calcium acetate solution was added to an ultrapure water (20 ml)-acetonitrile (5 ml) uniform solution of 104 mg (0.190 mmol) of sodium (R)-1-{4'-[5-chloro-3-({[1-(thiophen-3-yl)ethoxy]carbonyl}amino)thiophen-2-yl]-[1,1'-biphenyl]-4-yl}cyclopropanecarboxylate obtained in Example 10. The mixture was stirred at room temperature for 2 days. The resultant suspension was filtered through a membrane filter (Millipore). The residue was washed with small amounts of acetonitrile and ultrapure water and was dried by vacuum heating to give the title compound weighing 47.8 mg (0.079 mmol, yield 48%) as a white solid. Mass spectrum (ESI+, m/z): 1085 [2M+1]+.

$^1$H-NMR spectrum (400 MHz, DMSO-d$_6$) δ: 9.32 (1H, brs), 7.74-7.64 (2H, m), 7.59-7.49 (5H, m), 7.47-7.40 (1H, m), 7.40-7.34 (2H, m), 7.22-7.16 (1H, m), 7.16-7.08 (1H, m), 5.82 (1H, q, J=6.4 Hz), 1.62-1.40 (3H, m), 1.40-1.20 (2H, m), 0.90-0.78 (2H, m).

Example 13

Sodium (R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylate (Compound No. I-26)

[Chem. 36]

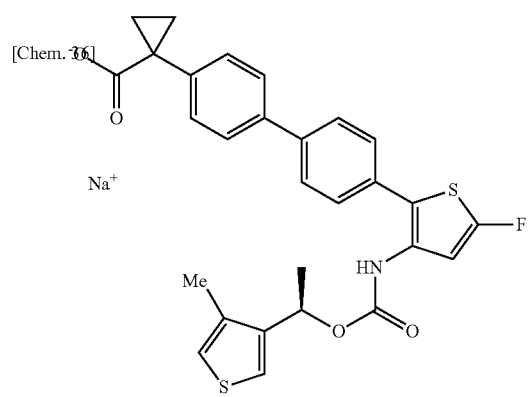

In an ice bath and while performing stirring, 2.00 ml (2.00 mmol) of a 1N aqueous sodium hydroxide solution was added to an acetonitrile (80 ml)-ultrapure water (6 ml) suspension of 1.04 g (2.00 mmol) of (R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylic acid synthesized in analogy to Reference Example 30. Acetonitrile (80 ml) and tetrahydrofuran (50 ml) were further added to the reaction mixture liquid, and the resultant mixture was ultrasonicated at room temperature for 30 minutes and was stirred at the temperature for 25 hours. The resultant suspension was filtered, and the residue was dried by vacuum heating to give the title compound weighing 760 mg (1.40 mmol, yield 70%) as a white solid.

Mass spectrum (ESI+, m/z): 544 [M+1]+.

$^1$H-NMR spectrum (400 MHz, DMSO-d$_6$) δ: 9.33 (1H, brs), 7.69-7.63 (2H, m), 7.54-7.39 (5H, m), 7.35-7.29 (2H, m), 7.16 (1H, d, J=1.9 Hz), 6.83 (1H, brs), 5.74 (1H, q, J=6.5 Hz), 2.17 (3H, s), 1.59-1.43 (3H, m), 1.18 (2H, dd, J=5.8, 2.8 Hz), 0.68 (2H, dd, J=5.8, 2.8 Hz).

Example 14

Potassium (R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylate (Compound No. I-28)

[Chem. 37]

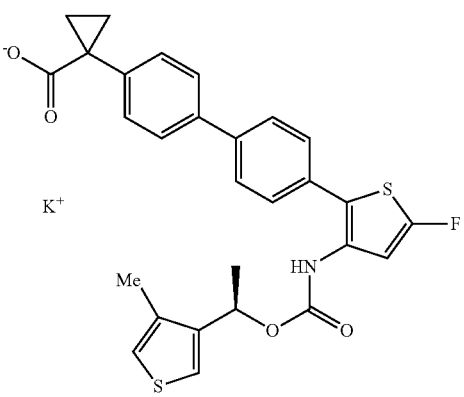

At room temperature and while performing stirring, 0.500 ml (0.500 mmol) of a 1N aqueous potassium hydroxide solution was added to an acetonitrile (20 ml)-tetrahydrofuran (5 ml) uniform solution of 260 mg (0.499 mmol) of (R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylic acid synthesized in analogy to Reference Example 30. The mixture was ultrasonicated and was stirred at room temperature for 2 hours. The resultant suspension was filtered through a membrane filter (Millipore). The residue was washed with a small amount of acetonitrile and was dried by vacuum heating to give the title compound weighing 126 mg (0.226 mmol, yield 45%) as a white solid.

Mass spectrum (ESI+, m/z): 560 [M+1]+.

$^1$H-NMR spectrum (400 MHz, DMSO-d$_6$) δ: 9.34 (1H, brs), 7.69-7.63 (2H, m), 7.56-7.41 (5H, m), 7.34-7.27 (2H, m), 7.16 (1H, d, J=2.0 Hz), 6.83 (1H, brs), 5.74 (1H, q, J=6.5

Hz), 2.17 (3H, brs), 1.57-1.45 (3H, m), 1.14 (2H, dd, J=5.9, 2.8 Hz), 0.63 (2H, dd, J=5.8, 2.6 Hz).

Example 15

½ Calcium (R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylate (Compound No. I-30)

[Chem. 38]

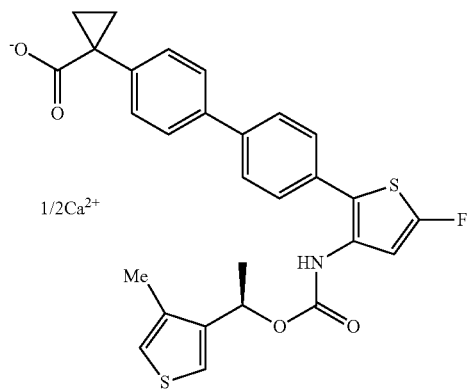

0.190 ml (0.095 mmol) of a 0.5 M aqueous calcium acetate solution was added to an ultrapure water (25 ml) uniform solution of 103 mg (0.190 mmol) of sodium (R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylate synthesized in analogy to Example 13. The mixture was stirred at room temperature for 2 days. The resultant suspension was filtered through a membrane filter (Millipore). The residue was washed with ultrapure water and was dried by vacuum heating to give the title compound weighing 27.7 mg (0.051 mmol, yield 27%) as a white solid.

Mass spectrum (ESI$^+$, m/z): 1081 [2M+1]$^+$.

$^1$H-NMR spectrum (400 MHz, DMSO-$d_6$) δ: 9.32 (1H, brs), 7.70-7.63 (2H, m), 7.57-7.31 (8H, m), 7.14 (1H, d, J=1.9 Hz), 6.82 (1H, brs), 5.74 (1H, q, J=6.5 Hz), 2.17 (3H, s), 1.61-1.41 (3H, m), 1.41-1.20 (2H, m), 0.91-0.78 (2H, m).

REFERENCE EXAMPLES

Reference Example 1

2-bromothiophene-3-carboxylic acid tert-butyl ester

[Chem. 39]

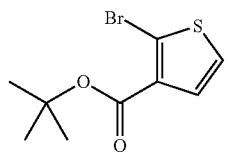

In a nitrogen atmosphere, 7.6 ml (87 mmol) of oxalyl chloride was added dropwise to a methylene chloride (70 ml) solution of 15 g (72 mmol) of 2-bromothiophene-3-carboxylic acid (Aldrich) and 0.60 ml (7.8 mmol) of N,N-dimethylformamide at room temperature while performing stirring. The mixture was stirred at the temperature for 15 hours. After the completion of the reaction, the reaction mixture liquid was concentrated under reduced pressure. 2-Methyl-2-propanol (70 ml), 65 ml (372 mmol) of N,N-diisopropylethylamine and 0.90 g (7.4 mmol) of N,N-dimethylaminopyridine were sequentially added to the residue. In a nitrogen atmosphere, the resultant mixture was stirred for 2 hours while performing heating at 80° C. After the completion of the reaction, the reaction mixture liquid was concentrated under reduced pressure. Water was added to the residue, and the mixture was extracted with toluene. The organic phase was washed with saturated brine, dried with anhydrous magnesium sulfate, and concentrated under reduced pressure. The residue was subjected to silica gel column chromatography (eluting solvent: hexane:ethyl acetate=100:0 to 90:10 (V/V)), and the fraction containing the target compound was concentrated under reduced pressure to give the title compound weighing 12 g (32 mmol (purity 71 wt %), yield 45%) as a light yellow oil.

Mass spectrum (EI, m/z): 262 [M]$^+$.

$^1$H-NMR spectrum (400 MHz, CDCl$_3$) δ: 7.32 (1H, d, J=5.8 Hz), 7.18 (1H, d, J=5.8 Hz), 1.59 (9H, s).

The title compound was also synthesized as follows.

In an argon atmosphere, 1.80 g (9.70 mmol) of p-toluenesulfonyl chloride was added in small portions to a pyridine (9.6 ml) solution of 1.005 g (4.85 mmol) of 2-bromothiophene-3-carboxylic acid (Aldrich) in an ice bath while performing stirring. Next, 0.46 ml (4.8 mmol) of 2-methyl-2-propanol was added. In an ice bath, the mixture was stirred for 2 hours. Stirring was further performed at room temperature for 1 hour. Thereafter, 0.47 ml (5.0 mmol) of 2-methyl-2-propanol was added, and the mixture was stirred at room temperature for 27 hours. After the completion of the reaction, the reaction mixture liquid was concentrated under reduced pressure. Ethyl acetate and a saturated aqueous sodium hydrogencarbonate solution were added to perform liquid separation. The organic phase was washed with a saturated aqueous sodium hydrogencarbonate solution and subsequently with saturated brine. Further, the organic phase was washed with a 5 wt % aqueous potassium hydrogensulfate solution and was washed with saturated brine again. The organic phase was dried with anhydrous magnesium sulfate and was concentrated under reduced pressure. The residue was subjected to silica gel column chromatography (eluting solvent: hexane:ethyl acetate=99:1 to 94:6 (V/V)), and the fraction containing the target compound was concentrated under reduced pressure to give the title compound weighing 1.22 g (4.64 mmol, yield 96%) as a light yellow oil.

$^1$H-NMR spectrum (400 MHz, DMSO-$d_6$) δ: 7.63 (1H, d, J=5.8 Hz), 7.28 (1H, d, J=5.8 Hz), 1.53 (9H, s).

Reference Example 2

2-Bromo-5-chlorothiophene-3-carboxamide

[Chem. 40]

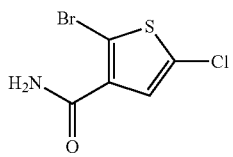

In an argon atmosphere and while performing stirring, 8.70 g (65.2 mmol) of N-chlorosuccinimide was added to an N,N-dimethylformamide (50 ml) solution of 4.48 g (21.7 mmol) of 2-bromothiophene-3-carboxamide (synthesized in accordance with WO 10/036497). The mixture was stirred for 3 hours while performing heating at 60° C. After the completion of the reaction, 50 ml of water and 100 ml of ethyl acetate were added thereto in an ice bath. While performing stirring, 6.80 g (65.3 mmol) of sodium hydrogensulfite was added. The mixture was stirred at room temperature for 15 minutes. Thereafter, water was added to perform liquid separation. The organic phase was washed two times with 50 ml of a saturated aqueous sodium hydrogencarbonate solution. The organic phase was then washed with saturated brine and was dried with anhydrous magnesium sulfate. The solvent was concentrated under reduced pressure to about half the volume. Hexane was added to the resultant suspension, and the mixture was ultrasonicated. Subsequently, the solid was collected by filtration, washed with hexane and dried by vacuum heating to give the title compound weighing 3.64 g (15.1 mmol, yield 70%) as a white solid.

Mass spectrum (DUIS+, m/z): 240 [M+1]+.
$^1$H-NMR spectrum (400 MHz, DMSO-$d_6$) δ: 7.75 (1H, brs), 7.58 (1H, brs), 7.33 (1H, s).

The title compound was also synthesized as follows.

In a nitrogen atmosphere, 0.90 g (6.7 mmol) of N-chlorosuccinimide was added to an N,N-dimethylformamide (16 ml) solution of 1.0 g (4.8 mmol) of 2-bromothiophene-3-carboxylic acid (Aldrich) at room temperature while performing stirring. The mixture was stirred for 1 hour while performing heating at 80° C. After the completion of the reaction, the reaction mixture liquid was allowed to cool. Water was added, and the liquid was acidified by the addition of 2N hydrochloric acid. The mixture was extracted with ethyl acetate. The organic phase was washed sequentially with an aqueous sodium hydrogensulfite solution and saturated brine, dried with anhydrous magnesium sulfate, and concentrated under reduced pressure. The residue was dissolved in methylene chloride (15 ml), and 0.80 ml (9.1 mmol) of oxalyl chloride was added dropwise to the solution in a nitrogen atmosphere at 0° C. while performing stirring. The temperature was raised to room temperature, and the mixture was stirred for 30 minutes. Next, 3.7 ml (48 mmol) of 28 wt % aqueous ammonia was added dropwise at room temperature while performing stirring, and the mixture was stirred at room temperature for 1 hour. After the completion of the reaction, water was added to the reaction mixture liquid, and the mixture was extracted with ethyl acetate. The organic phase was washed with saturated brine, dried anhydrous magnesium sulfate, and concentrated under reduced pressure. The residue was subjected to silica gel column chromatography (eluting solvent: hexane:ethyl acetate=69:31 to 48:52 (V/V)), and the fraction containing the target compound was concentrated under reduced pressure and was dried by vacuum heating to give the title compound weighing 0.62 g (2.6 mmol, yield 53%) as a white solid.

Reference Example 3

4-Bromo-1-iodo-2-methoxybenzene

[Chem. 41]

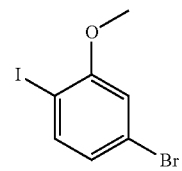

In an ice bath and while performing stirring, 0.75 g (11 mmol) of sodium nitrite was added to an acetic acid (15 ml)-concentrated hydrochloric acid (1 ml) solution of 2.0 g (9.0 mmol) of 4-bromo-2-methoxyaniline (Tokyo Chemical Industry Co., Ltd.) in such a manner that the inside temperature did not exceed 10° C. The mixture was stirred at room temperature for 30 minutes. Next, the reaction mixture liquid was added dropwise to an aqueous solution of 1.0 g (30 mmol) of potassium iodide in a 48 wt % aqueous hydrobromic acid solution (30 ml) at room temperature while performing stirring. The resultant mixture was stirred at the temperature for 1 hour. After the completion of the reaction, the reaction mixture liquid was added in small portions to a mixture of an aqueous sodium carbonate solution and methylene chloride. After the basicity of the aqueous phase was confirmed, the liquid was separated. The organic phase was washed sequentially with a 10 wt % aqueous sodium hydrogensulfite solution, a saturated aqueous sodium hydrogencarbonate solution and saturated brine, dried with anhydrous magnesium sulfate, and concentrated under reduced pressure. The residue was subjected to silica gel column chromatography (eluting solvent: hexane:ethyl acetate=100:0 to 91:9 (V/V)), and the fraction containing the target compound was concentrated under reduced pressure to give the title compound weighing 2.2 g (7.2 mmol, yield 73%) as an orange solid.

Mass spectrum (EI, m/z): 312 [M]+.
$^1$H-NMR spectrum (400 MHz, CDCl$_3$) δ: 7.61 (1H, d, J=8.3 Hz), 6.94 (1H, d, J=2.1 Hz), 6.87 (1H, dd, J=8.2, 2.1 Hz), 3.88 (3H, s).

Reference Example 4

1-(4'-bromo-2'-methoxy-[1,1'-biphenyl]-4-yl)cyclopropanecarboxylic acid ethyl ester

[Chem. 42]

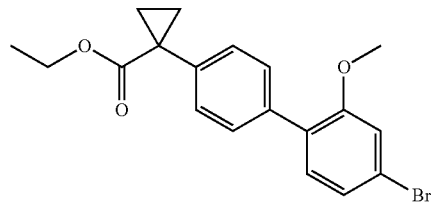

A 1,4-dioxane (15 ml)-water (10 ml) solution of 1.2 g (3.8 mmol) of 4-bromo-1-iodo-2-methoxybenzene synthesized in analogy to Reference Example 3, 1.1 g (3.5 mmol) of 1-[4-(4,4,5,5-tetramethyl-1,3,2-dioxaborolan-2-yl)phenyl]cyclopropanecarboxylic acid ethyl ester (synthesized in accordance with the process described in WO 12/078593) and 1.1 g (10 mmol) of sodium carbonate was degassed and was purged with nitrogen. Next, 0.10 g (0.12 mmol) of [1,1'-bis(diphenylphosphino)ferrocene]palladium (II) dichloride methylene chloride adduct was added. The mixture was stirred in a nitrogen atmosphere for 1.5 hours while performing heating at 80° C. After the completion of the reaction, water was added to the reaction mixture liquid, and the mixture was extracted with ethyl acetate. The organic phase was washed with saturated brine, dried with anhydrous magnesium sulfate, and concentrated under reduced pressure. The residue was subjected to silica gel column chromatography (eluting solvent: hexane:ethyl acetate=94:6 to 75:25 (V/V)), and the fraction containing the target compound was concentrated under reduced pressure and was dried by vacuum heating to give the title compound weighing 0.72 g (1.9 mmol, yield 55%) as a white solid.

Mass spectrum (EI, m/z): 374 [M]+.

$^1$H-NMR spectrum (400 MHz, CDCl$_3$) δ: 7.45-7.41 (2H, m), 7.39-7.35 (2H, m), 7.19 (1H, d, J=8.0 Hz), 7.15 (1H, dd, J=8.0, 1.8 Hz), 7.10 (1H, d, J=1.8 Hz), 4.12 (2H, q, J=7.1 Hz), 3.81 (3H, s), 1.61 (2H, dd, J=7.0, 4.0 Hz), 1.22 (2H, dd, J=7.0, 4.0 Hz), 1.19 (3H, t, J=7.1 Hz).

Reference Example 5

1-(4'-chloro-2'-methoxy-[1,1'-biphenyl]-4-yl)cyclopropanecarboxylic acid ethyl ester

[Chem. 43]

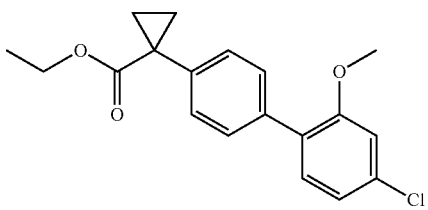

A 1,4-dioxane (20 ml)-water (20 ml) solution of 2.0 g (9.0 mmol) of 1-bromo-4-chloro-2-methoxybenzene (Tokyo Chemical Industry Co., Ltd.), 2.6 g (8.2 mmol) of 1-[4-(4,4,5,5-tetramethyl-1,3,2-dioxaborolan-2-yl)phenyl]cyclopropanecarboxylic acid ethyl ester (synthesized in accordance with the process described in WO 12/078593) and 2.7 g (25 mmol) of sodium carbonate was degassed and was purged with nitrogen. Next, 0.21 g (0.25 mmol) of [1,1'-bis(diphenylphosphino)ferrocene]palladium (II) dichloride methylene chloride adduct was added. The mixture was stirred in a nitrogen atmosphere for 2 hours while performing heating at 80° C. After the completion of the reaction, water was added to the reaction mixture liquid, and the mixture was extracted with ethyl acetate. The organic phase was washed with saturated brine, dried with anhydrous magnesium sulfate, and concentrated under reduced pressure. The residue was subjected to silica gel column chromatography, and the fraction having Rf=0.5 (developing solvent: hexane:ethyl acetate=90:10 (V/V)) was concentrated under reduced pressure and was dried by vacuum heating to give the title compound weighing 2.46 g (7.4 mmol, yield 90%) as a white solid.

Mass spectrum (EI, m/z): 330 [M]+.

$^1$H-NMR spectrum (400 MHz, CDCl$_3$) δ: 7.45-7.41 (2H, m), 7.39-7.35 (2H, m), 7.25 (1H, d, J=8.2 Hz), 7.00 (1H, dd, J=8.2, 2.0 Hz), 6.96 (1H, d, J=2.0 Hz), 4.12 (2H, q, J=7.1 Hz), 3.81 (3H, s), 1.61 (2H, dd, J=6.9, 3.9 Hz), 1.22 (2H, dd, J=7.0, 4.0 Hz), 1.19 (3H, t, J=7.1 Hz).

Reference Example 6

1-[2'-methoxy-4'-(4,4,5,5-tetramethyl-1,3,2-dioxaborolan-2-yl)-[1,1'-biphenyl]-4-yl]cyclopropanecarboxylic acid ethyl ester

[Chem. 44]

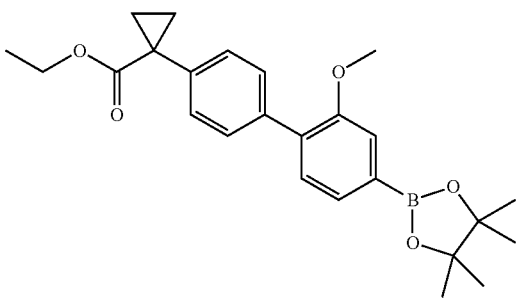

A 1,4-dioxane (10 ml) solution of 0.72 g (1.9 mmol) of 1-(4'-bromo-2'-methoxy-[1,1'-biphenyl]-4-yl)cyclopropanecarboxylic acid ethyl ester synthesized in analogy to Reference Example 4, 0.60 g (2.4 mmol) of 4,4,4',4',5,5,5',5'-octamethyl-2,2'-bi(1,3,2-dioxaborolane) and 0.30 g (3.1 mmol) of potassium acetate was degassed and was purged with nitrogen. Next, 0.10 g (0.12 mmol) of [1,1'-bis(diphenylphosphino)ferrocene]palladium (II) dichloride methylene chloride adduct was added. In a nitrogen atmosphere, the mixture was stirred for 3 hours while performing heating under reflux conditions. After the completion of the reaction, water was added to the reaction mixture liquid, and the mixture was extracted with toluene. The organic phase was washed with saturated brine, dried with anhydrous magnesium sulfate, and concentrated under reduced pressure. The residue was subjected to silica gel column chromatography (eluting solvent: hexane:ethyl acetate=92:8 to 79:21 (V/V)), and the fraction containing the target compound was concentrated under reduced pressure and was dried by vacuum heating to give the title compound weighing 0.81 g (1.9 mmol, quantitative yield) as a light yellow solid.

Mass spectrum (EI, m/z): 422 [M]+.

$^1$H-NMR spectrum (400 MHz, CDCl$_3$) δ: 7.52-7.46 (3H, m), 7.40-7.33 (4H, m), 4.12 (2H, q, J=7.1 Hz), 3.86 (3H, s), 1.60 (2H, dd, J=6.9, 3.9 Hz), 1.36 (12H, s), 1.22 (2H, dd, J=7.0, 4.0 Hz), 1.19 (3H, t, J=7.1 Hz).

The title compound was also synthesized as follows.

A 1,4-dioxane (30 ml) solution of 2.46 g (7.43 mmol) of 1-(4'-chloro-2'-methoxy-[1,1'-biphenyl]-4-yl)cyclopropanecarboxylic acid ethyl ester synthesized in analogy to Reference Example 5, 2.43 g (9.57 mmol) of 4,4,4',4',5,5,5',5'-octamethyl-2,2'-bi(1,3,2-dioxaborolane) and 1.1 g (11 mmol) of potassium acetate was degassed and was purged with nitrogen. Next, 0.30 g (0.37 mmol) of [1,1'-bis(diphenylphosphino)ferrocene]palladium (II) dichloride methylene chloride adduct and 0.30 g (1.1 mmol) of tricyclohexylphosphine were added. The mixture was stirred in a nitrogen atmosphere for 24 hours while performing heating under reflux conditions. Further, 0.15 g (0.18 mmol) of [1,1'-bis(diphenylphosphino)ferrocene]palladium (II) dichloride methylene chloride adduct and 0.15 g (0.54 mmol) of tricyclohexylphosphine were added to the reaction mixture liquid, and the mixture was stirred in a nitrogen atmosphere for 5 hours while performing heating under reflux conditions. After the completion of the reaction, the reaction mixture liquid was cooled to room temperature. Toluene was added, and insoluble matters were filtered out. The filtrate was washed sequentially with a saturated aqueous sodium hydrogencarbonate solution and saturated brine, dried with anhydrous magnesium sulfate and concentrated under reduced pressure. The residue was subjected to silica gel column chromatography (eluting solvent: hexane:ethyl acetate=92:8 to 79:21 (V/V)), and the fraction containing the target compound was concentrated under reduced pressure. Hexane was added to the residue. The solid was collected by filtration, washed with hexane and dried by vacuum heating to give the title compound weighing 1.89 g (4.5 mmol, yield 60%) as a white solid.

Reference Example 7

1-[4'-(3-carbamoyl-5-chlorothiophen-2-yl)-[1,1'-biphenyl]-4-yl]cyclopropanecarboxylic acid ethyl ester

[Chem. 45]

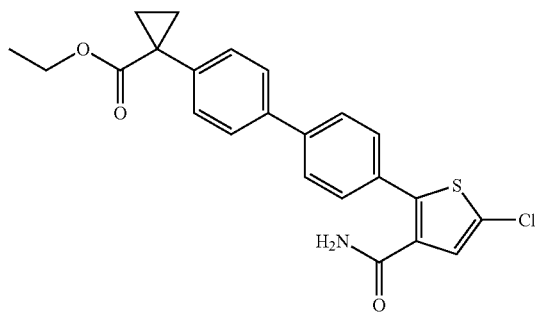

A 1,4-dioxane (15 ml)-water (5 ml) solution of 486 mg (2.02 mmol) of 2-bromo-5-chlorothiophene-3-carboxamide synthesized in analogy to Reference Example 2, 877 mg (2.23 mmol) of 1-[4'-(4,4,5,5-tetramethyl-1,3,2-dioxaborolan-2-yl)-[1,1'-biphenyl]-4-yl]cyclopropanecarboxylic acid ethyl ester (synthesized in accordance with the process described in WO 12/078593) and 658 mg (6.21 mmol) of sodium carbonate was freeze degassed in a dry ice-acetone bath and was purged with argon. Further, 230 mg (0.199 mmol) of tetrakis(triphenylphosphine)palladium (0) was added, and the mixture was stirred for 3 hours while performing heating at 90° C. After the completion of the reaction, the reaction mixture liquid was cooled. Ethyl acetate and water were added to perform liquid separation. The organic phase was dried with anhydrous magnesium sulfate and was concentrated under reduced pressure. The residue was subjected to silica gel column chromatography (eluting solvent: hexane:ethyl acetate=64:36 to 43:57 (V/V)), and the fraction containing the target compound was concentrated under reduced pressure. A hexane-ethyl acetate (2:1 (V/V)) solution was added to the residue, and the solid precipitated was collected by filtration and was dried by vacuum heating to give the title compound weighing 705 mg (1.66 mmol, yield 82%) as a white solid.

Mass spectrum (EI, m/z): 425 [M]+.

$^1$H-NMR spectrum (400 MHz, CDCl$_3$) δ: 7.69-7.65 (2H, m), 7.58-7.53 (4H, m), 7.46-7.42 (2H, m), 7.33 (1H, s), 5.44 (2H, brs), 4.12 (2H, q, J=7.1 Hz), 1.65 (2H, dd, J=7.0, 4.0 Hz), 1.23 (2H, dd, J=7.0, 4.0 Hz), 1.19 (3H, t, J=7.1 Hz).

Reference Example 8

1-[4'-(3-carbamoyl-5-chlorothiophen-2-yl)-2'-methoxy-[1,1'-biphenyl]-4-yl]cyclopropanecarboxylic acid ethyl ester

[Chem. 46]

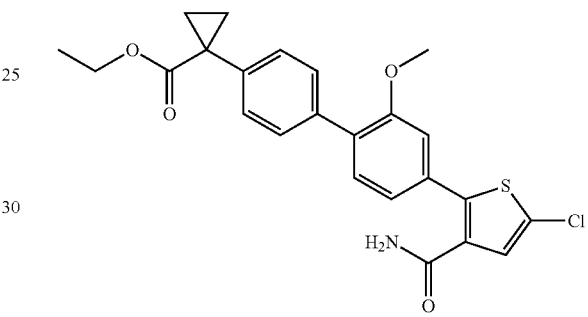

A 1,4-dioxane (30 ml)-water (10 ml) solution of 2.0 g (4.7 mmol) of 1-[2'-methoxy-4'-(4,4,5,5-tetramethyl-1,3,2-dioxaborolan-2-yl)-[1,1'-biphenyl]-4-yl]-cyclopropanecarboxylic acid ethyl ester synthesized in analogy to Reference Example 6, 1.25 g (5.2 mmol) of 2-bromo-5-chlorothiophene-3-carboxamide synthesized in analogy to Reference Example 2 and 1.5 g (14 mmol) of sodium carbonate was degassed. Next, 0.30 g (0.26 mmol) of tetrakis(triphenylphosphine)palladium (0) was added. The mixture was stirred in a nitrogen atmosphere for 4.5 hours while performing heating at 90° C. After the completion of the reaction, the reaction mixture liquid was allowed to cool. Water was added, and the mixture was extracted with ethyl acetate. The organic phase was washed with saturated brine, dried with anhydrous magnesium sulfate, and concentrated under reduced pressure. Ethyl acetate was added to the residue. The solid was collected by filtration, washed with a small amount of ethyl acetate and dried by vacuum heating to give the title compound weighing 1.53 g (3.4 mmol, yield 71%) as a white solid.

Mass spectrum (EI, m/z): 455 [M]+.

$^1$H-NMR spectrum (400 MHz, DMSO-d$_6$) δ: 7.73 (1H, brs), 7.50 (1H, brs), 7.48-7.43 (2H, m), 7.39-7.33 (3H, m), 7.32 (1H, s), 7.25 (1H, d, J=1.6 Hz), 7.13 (1H, dd, J=7.8, 1.6 Hz), 4.05 (2H, q, J=7.1 Hz), 3.79 (3H, s), 1.51 (2H, dd, J=6.8, 4.0 Hz), 1.23 (2H, dd, J=7.0, 4.0 Hz), 1.12 (3H, t, J=7.1 Hz).

Reference Example 9

2-{4'-[1-(ethoxycarbonyl)cyclopropyl]-[1,1'-biphenyl]-4-yl}thiophene-3-carboxylic acid tert-butyl ester

[Chem. 47]

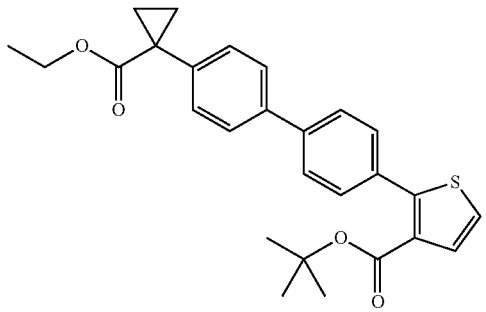

A 1,4-dioxane (15 ml)-water (5 ml) solution of 0.80 g (2.0 mmol) of 1-[4'-(4,4,5,5-tetramethyl-1,3,2-dioxaborolan-2-yl)-[1,1'-biphenyl]-4-yl]cyclopropane carboxylic acid ethyl ester (synthesized in accordance with the process described in WO 12/078593), 0.50 g (1.9 mmol) of 2-bromothiophene-3-carboxylic acid tert-butyl ester synthesized in analogy to Reference Example 1 and 0.61 g (5.8 mmol) of sodium carbonate was degassed. Next, 0.10 g (0.089 mmol) of tetrakis(triphenylphosphine)palladium (0) was added. The mixture was stirred in a nitrogen atmosphere for 14.5 hours while performing heating at 90° C. After the completion of the reaction, the reaction mixture liquid was allowed to cool. Water was added, and the mixture was extracted with ethyl acetate. The organic phase was washed with saturated brine, dried with anhydrous magnesium sulfate, and concentrated under reduced pressure. The residue was subjected to silica gel column chromatography, and the fraction having Rf=0.41 (developing solvent: hexane:ethyl acetate=90:10 (V/V)) was concentrated under reduced pressure and was dried by vacuum heating to give the title compound weighing 0.58 g (1.3 mmol, yield 68%) as a white solid.

Mass spectrum (EI, m/z): 448 [M]$^+$.

$^1$H-NMR spectrum (400 MHz, CDCl$_3$) δ: 7.64-7.60 (2H, m), 7.59-7.55 (2H, m), 7.55-7.51 (2H, m), 7.48 (1H, d, J=5.4 Hz), 7.45-7.41 (2H, m), 7.23 (1H, d, J=5.3 Hz), 4.13 (2H, q, J=7.1 Hz), 1.64 (2H, dd, J=6.9, 3.9 Hz), 1.38 (9H, s), 1.23 (2H, dd, J=7.2, 4.1 Hz), 1.20 (3H, t, J=7.2 Hz).

Reference Example 10

2-{4'-[1-(ethoxycarbonyl)cyclopropyl]-2-methoxy-[1,1'-biphenyl]-4-yl}thiophene-3-carboxylic acid tert-butyl ester

[Chem. 48]

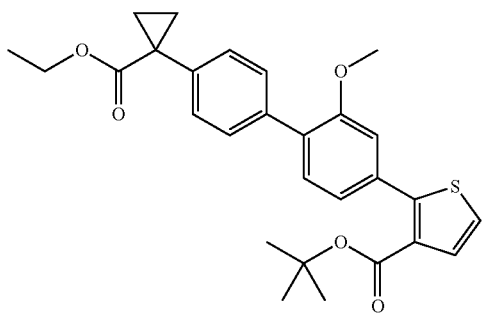

2.96 g (27.9 mmol) of sodium carbonate was added to a 1,4-dioxane (23 ml)-water (23 ml) solution of 3.81 g (9.02 mmol) of 1-[2'-methoxy-4'-(4,4,5,5-tetramethyl-1,3,2-dioxaborolan-2-yl)-[1,1'-biphenyl]-4-yl]-cyclopropanecarboxylic acid ethyl ester synthesized in analogy to Reference Example 6 and 2.7 g (7.3 mmol (purity 71 wt %)) of 2-bromothiophene-3-carboxylic acid tert-butyl ester synthesized in Reference Example 1. The mixture was degassed. Next, 540 mg (0.467 mmol) of tetrakis(triphenylphosphine) palladium (0) was added. The resultant mixture was stirred in a nitrogen atmosphere for 7 hours while performing heating at 90° C. After the completion of the reaction, the reaction mixture liquid was allowed to cool. Water was added, and the mixture was extracted with ethyl acetate. The organic phase was washed with saturated brine, dried with anhydrous magnesium sulfate, and concentrated under reduced pressure. Ethyl acetate was added to the residue. The resultant insoluble matters were removed by filtration and were washed with a hexane-ethyl acetate (1:2 (V/V)) mixture solution. Subsequently, the mother liquor and the washings were combined and concentrated under reduced pressure. The concentrate was dissolved in ethyl acetate, and hexane was added until the solution became cloudy. The solid precipitated was filtered off, washed with hexane and dried by vacuum heating to give the title compound weighing 3.09 g (5.55 mmol (purity 86 wt %), yield 61%) as a white solid.

Mass spectrum (EI, m/z): 478 [M]$^+$.

$^1$H-NMR spectrum (400 MHz, CDCl$_3$) δ: 7.53-7.48 (2H, m), 7.47 (1H, d, J=5.4 Hz), 7.41-7.36 (2H, m), 7.34 (1H, d, J=7.8 Hz), 7.23 (1H, d, J=5.4 Hz), 7.12 (1H, dd, J=7.7, 1.6 Hz), 7.07 (1H, d, J=1.6 Hz), 4.13 (2H, q, J=7.1 Hz), 3.83 (3H, s), 1.62 (2H, dd, J=6.8, 4.0 Hz), 1.40 (9H, s), 1.23 (2H, dd, J=6.8, 3.8 Hz), 1.20 (3H, t, J=7.1 Hz).

Reference Example 11

2-{4'-[1-(ethoxycarbonyl)cyclopropyl]-[1,1'-biphenyl]-4-yl}-5-fluorothiophene-3carboxylic acid tert-butyl ester

[Chem. 49]

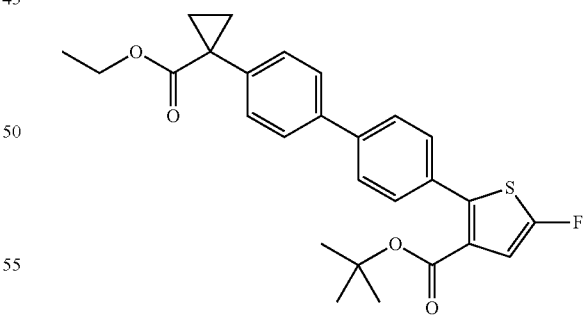

In an argon atmosphere, 11 ml (12.0 mmol) of a 1.09 M tetrahydrofuran-hexane solution of lithium diisopropylamide (Kanto Chemical Co., Inc.) was added dropwise over a period of 5 minutes to a dehydrated tetrahydrofuran (60 ml) solution of 4.50 g (10.0 mmol) of 2-{4'-[1-(ethoxycarbonyl)cyclopropyl]-[1,1'-biphenyl]-4-yl}thiophene-3-carboxylic acid tert-butyl ester synthesized in analogy to Reference Example 9 while cooling the system to −70° C. or below in a dry ice-acetone bath. The mixture was stirred at the temperature for 30 minutes. Next, while cooling the system to −65° C. or below, a tetrahydrofuran (15 ml) solution of 4.75 g (15.1 mmol) of N-fluorobenzenesulfonimide was added dropwise over a period of 5 minutes, and the mixture was stirred at the temperature for 30 minutes. Next, the temperature was gradually raised, and the reaction was terminated at −45° C. by the addition of 40 ml of a saturated aqueous ammonium chloride solution. The temperature was raised to room temperature, and the mixture was extracted with ethyl acetate. The organic phase was dried with anhydrous magnesium sulfate and was concentrated under reduced pressure. Methylene chloride was added to the residue. Insoluble matters was filtered out, and the filtrate was concentrated under reduced pressure. The residue was subjected to silica gel column chromatography (eluting solvent: hexane:ethyl acetate=100:0 to 79:21 (V/V)), and the fraction containing the target compound was concentrated under reduced pressure and was dried by vacuum heating to give the title compound weighing 2.23 g (4.78 mmol, yield 48%) as a white solid.

Mass spectrum (CI, m/z): 467 [M+1]$^+$.

$^1$H-NMR spectrum (400 MHz, DMSO-d$_6$) δ: 7.78-7.72 (2H, m), 7.68-7.63 (2H, m), 7.56-7.50 (2H, m), 7.46-7.41 (2H, m), 7.03 (1H, d, J=2.4 Hz), 4.05 (2H, q, J=7.1 Hz), 1.52 (2H, dd, J=6.9, 3.9 Hz), 1.31 (9H, s), 1.24 (2H, dd, J=7.1, 4.1 Hz), 1.12 (3H, t, J=7.1 Hz).

Reference Example 12

2-{4'-[1-(ethoxycarbonyl)cyclopropyl]-2-methoxy-[1,1'-biphenyl]-4-yl}-5-fluorothiophene-3-carboxylic acid tert-butyl ester

[Chem. 50]

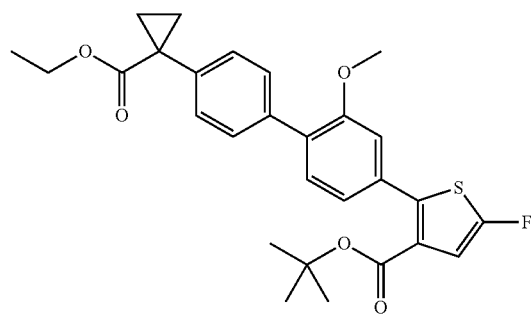

In an argon atmosphere, 6.56 ml (7.22 mmol) of a 1.1 M lithium diisopropylamide/tetrahydrofuran solution was added dropwise to a tetrahydrofuran (37 ml) solution of 2.88 g (5.17 mmol (purity 86 wt %)) of 2-{4'-[1-(ethoxycarbonyl)cyclopropyl]-2-methoxy-[1,1'-biphenyl]-4-yl}thiophene-3-carboxylic acid tert-butyl ester synthesized in Reference Example 10, at −78° C. while performing stirring. The mixture was stirred at the temperature for 30 minutes. Next, a tetrahydrofuran (9.5 ml) solution of 2.85 g (9.04 mmol) of N-fluorobenzenesulfonimide was added dropwise, and the mixture was stirred at the temperature for 30 minutes. After the completion of the reaction, a saturated aqueous ammonium chloride solution and ethyl acetate were added to the reaction mixture liquid. The organic phase was separated. The organic phase was washed with saturated brine, dried with anhydrous magnesium sulfate, and concentrated under reduced pressure. The residue was subjected to silica gel column chromatography (eluting solvent: hexane:dichloroethane=100:0 to 30:70 (V/V)), and the fraction containing the target compound was concentrated under reduced pressure. Hexane was added to the residue, and the mixture was heated to give a solution, which was ultrasonicated. The solid precipitated was collected by filtration, washed with hexane and dried by vacuum heating to give the title compound weighing 496 mg (1.00 mmol, yield 20%) as a white solid.

Mass spectrum (DUIS$^+$, m/z): 497 [M+1]$^+$.

$^1$H-NMR spectrum (400 MHz, CDCl$_3$) δ: 7.52-7.46 (2H, m), 7.41-7.36 (2H, m), 7.33 (1H, d, J=7.8 Hz), 7.08 (1H, dd, J=7.8, 1.6 Hz), 7.03 (1H, d, J=1.5 Hz), 6.84 (1H, d, J=2.3 Hz), 4.13 (2H, q, J=7.1 Hz), 3.82 (3H, s), 1.62 (2H, dd, J=6.9, 3.9 Hz), 1.37 (9H, s), 1.23 (2H, dd, J=6.5, 3.5 Hz), 1.20 (3H, t, J=7.2 Hz).

Reference Example 13

2-{4'-[1-(Ethoxycarbonyl)cyclopropyl]-[1,1'-biphenyl]-4-yl}-5-fluorothiophene-3-carboxylic acid

[Chem. 51]

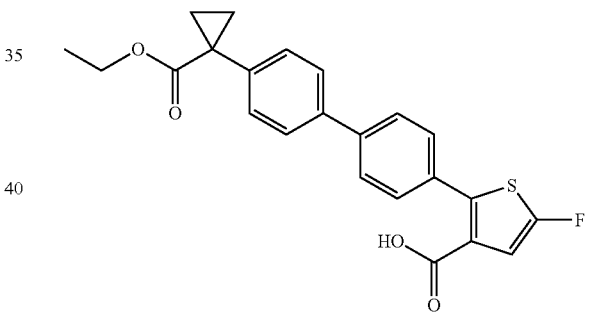

In an argon atmosphere, 5.0 ml (65 mmol) of trifluoroacetic acid was added to a methylene chloride (20 ml) solution of 2.18 g (4.67 mmol) of 2-{4'-[1-(ethoxycarbonyl)cyclopropyl]-[1,1'-biphenyl]-4-yl}-5-fluorothiophene-3-carboxylic acid tert-butyl ester synthesized in analogy to Reference Example 11, in an ice bath while performing stirring. The mixture was stirred at the temperature for 1 hour and further at room temperature for 2 hours. After the completion of the reaction, the mixture was concentrated under reduced pressure. The residue was washed sequentially with diethyl ether and hexane, and was dried by vacuum heating to give the title compound weighing 1.87 g (4.56 mmol, yield 98%) as a white solid.

Mass spectrum (CI, m/z): 411 [M+1]$^+$.

$^1$H-NMR spectrum (400 MHz, DMSO-d$_6$) δ: 12.92 (1H, s), 7.74-7.70 (2H, m), 7.68-7.64 (2H, m), 7.60-7.55 (2H, m), 7.46-7.41 (2H, m), 7.05 (1H, d, J=2.4 Hz), 4.05 (2H, q, J=7.1 Hz), 1.52 (2H, dd, J=6.9, 3.9 Hz), 1.24 (2H, dd, J=7.0, 4.1 Hz), 1.11 (3H, t, J=7.1 Hz).

Reference Example 14

2-{4'-[1-(Ethoxycarbonyl)cyclopropyl]-2-methoxy-[1,1'-biphenyl]-4-yl}-5-fluorothiophene-3-carboxylic acid

[Chem. 52]

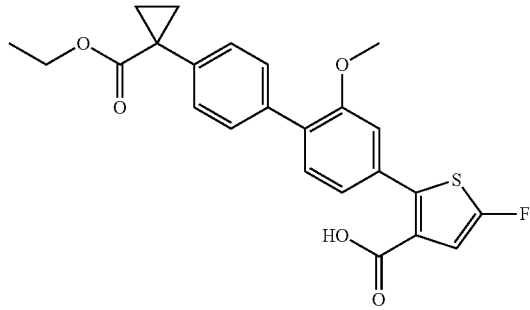

In an argon atmosphere at room temperature, 1.1 ml (14 mmol) of trifluoroacetic acid was added to a methylene chloride (4.4 ml) solution of 491 mg (0.989 mmol) of 2-{4'-[1-(ethoxycarbonyl)cyclopropyl]-2-methoxy-[1,1'-biphenyl]-4-yl}-5-fluorothiophene-3-carboxylic acid tert-butyl ester synthesized in analogy to Reference Example 12. The mixture was stirred at room temperature for 3 hours. After the completion of the reaction, the reaction mixture liquid was concentrated under reduced pressure. Methylene chloride was added, and the mixture was concentrated under reduced pressure. Hexane was added to the residue, and the mixture was concentrated under reduced pressure and was dried by vacuum heating to give the title compound weighing 436 mg (0.99 mmol, quantitative yield) as a white solid.

Mass spectrum (EI, m/z): 440 [M]$^+$.

$^1$H-NMR spectrum (400 MHz, CDCl$_3$) δ: 7.53-7.48 (2H, m), 7.40-7.37 (2H, m), 7.34 (1H, d, J=7.8 Hz), 7.14 (1H, d, J=1.6 Hz), 7.13-7.10 (1H, m), 6.94 (1H, d, J=2.3 Hz), 4.12 (2H, q, J=7.1 Hz), 3.82 (3H, s), 1.62 (2H, dd, J=6.9, 3.9 Hz), 1.23 (2H, dd, J=7.0, 4.0 Hz), 1.20 (3H, t, J=7.1 Hz).

Reference Example 15

1-[4'-(3-Carbamoyl-5-chlorothiophen-2-yl)-2'-methoxy-[1,1'-biphenyl]-4-yl]cyclopropanecarboxylic acid

[Chem. 53]

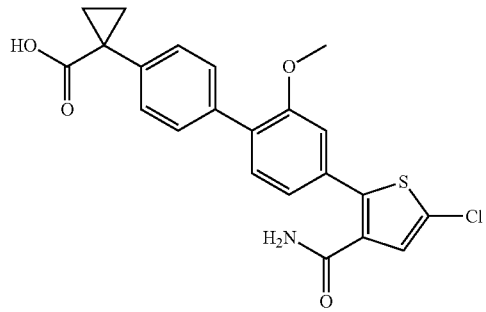

At room temperature and while performing stirring, 6.6 ml (6.6 mmol) of a 1N aqueous sodium hydroxide solution was added to an ethanol (10 ml)-tetrahydrofuran (10 ml) suspension of 1.00 g (2.19 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 8. The mixture was stirred at the temperature for 4 days. After the completion of the reaction, the reaction mixture liquid was neutralized by the addition of 6.6 ml (6.6 mmol) of 1N hydrochloric acid. Water was added, and the solid precipitated was filtered off through a membrane filter (Millipore), washed with water, and dried by vacuum heating to give the title compound weighing 884 mg (2.07 mmol, yield 94%) as a white solid.

Mass spectrum (DUIS$^+$, m/z): 428 [M+1]$^+$.

$^1$H-NMR spectrum (400 MHz, DMSO-d$_6$) δ: 12.35 (1H, brs), 7.75 (1H, brs), 7.52 (1H, brs), 7.45-7.41 (2H, m), 7.38-7.35 (2H, m), 7.33 (1H, d, J=7.9 Hz), 7.32 (1H, s), 7.24 (1H, d, J=1.8 Hz), 7.13 (1H, dd, J=7.8, 1.6 Hz), 3.79 (3H, s), 1.47 (2H, dd, J=6.7, 3.8 Hz), 1.18 (2H, dd, J=6.9, 3.9 Hz).

Reference Example 16

1-[4'-(3-carbamoyl-5-chlorothiophen-2-yl)-2'-methoxy-[1,1'-biphenyl]-4-yl]cyclopropanecarboxylic acid 2-(trimethylsilyl)ethyl ester

[Chem. 54]

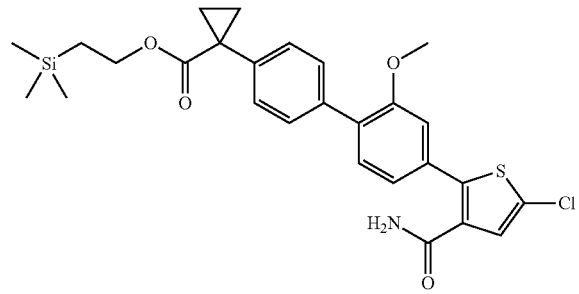

Toluene was added to 0.80 g (1.9 mmol) of 1-[4'-(3-carbamoyl-5-chlorothiophen-2-yl)-2'-methoxy-[1,1'-biphenyl]-4-yl]cyclopropanecarboxylic acid synthesized in Reference Example 15. After azeotropic dehydration was performed, the atmosphere was replaced by argon. Subsequently, there were added N,N-dimethylformamide (10 ml), 23.0 mg (0.188 mmol) of N,N-dimethylaminopyridine, 0.42 ml (2.8 mmol) of trimethylsilylethanol and 0.98 ml (5.6 mmol) of N,N-diisopropylethylamine. Next, in an ice bath, 1.06 g (2.81 mmol) of o-(benzotriazol-1-yl)-N,N,N',N'-tetramethyluronium hexafluorophosphate salt was added. The mixture was stirred at room temperature for 18 hours. Further, 64.6 mg (0.529 mmol) of N,N-dimethylaminopyridine was added to the reaction mixture liquid, and the mixture was stirred at the temperature for 1 day. After the completion of the reaction, water and ethyl acetate were added to the reaction mixture liquid. Extraction was performed two times with ethyl acetate. The organic phase was dried with anhydrous magnesium sulfate and was concentrated under reduced pressure. The residue was subjected to silica gel column chromatography (eluting solvent: hexane:ethyl acetate=71:29 to 50:50 (V/V)), and the fraction containing the target compound was concentrated under reduced pressure and was dried by vacuum heating to give the title compound weighing 889 mg (1.68 mmol, yield 90%) as a light yellow solid.

Mass spectrum (DUIS+, m/z): 528 [M+1]+.

1H-NMR spectrum (400 MHz, DMSO-d6) δ: 7.75 (1H, brs), 7.52 (1H, brs), 7.46-7.42 (2H, m), 7.38-7.34 (2H, m), 7.33 (1H, d, J=7.8 Hz), 7.32 (1H, s), 7.24 (1H, d, J=1.6 Hz), 7.13 (1H, dd, J=7.8, 1.7 Hz), 4.14-4.07 (2H, m), 3.78 (3H, s), 1.49 (2H, dd, J=6.8, 3.8 Hz), 1.22 (2H, dd, J=7.0, 4.1 Hz), 0.91-0.84 (2H, m), −0.05 (9H, s).

Reference Example 17

1-(4-Methylthiophen-3-yl)ethanone

[Chem. 55]

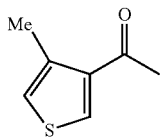

In an argon atmosphere at −78° C., 4.0 ml (6.4 mmol) of a 1.6 M hexane solution of n-butyllithium was added dropwise to a diethyl ether (23 ml) solution of 1.0 g (5.3 mmol) of 3-bromo-4-methylthiophene (Tokyo Chemical Industry Co., Ltd.). The mixture was stirred at the temperature for 15 minutes. Next, a diethyl ether (1 ml) solution of 0.70 ml (6.9 mmol) of N-methoxy-N-methylacetamide was added dropwise at −78° C., and the mixture was stirred at the temperature for 15 minutes and at room temperature for 23 hours. After the completion of the reaction, a saturated aqueous ammonium chloride solution was added to the reaction mixture liquid, and the resultant mixture was extracted with ethyl acetate. The organic phase was washed with water, dried with anhydrous magnesium sulfate, and concentrated under reduced pressure. The residue was subjected to silica gel column chromatography (eluting solvent: hexane:ethyl acetate=80:20 (V/V)), and the fraction containing the target compound was concentrated under reduced pressure to give the title compound weighing 552 mg (3.94 mmol, yield 75%) as a light yellow oil.

Mass spectrum (CI, m/z): 141 [M+1]+.

1H-NMR spectrum (400 MHz, CDCl3) δ: 7.99 (1H, d, J=3.1 Hz), 6.91 (1H, dq, J=3.1, 1.0 Hz), 2.53 (3H, s), 2.46 (3H, d, J=1.0 Hz).

Reference Example 18

(RS)-1-(2,5-difluorophenyl)ethanol

[Chem. 56]

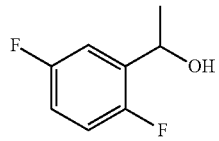

While performing stirring, 10 g (260 mmol) of sodium borohydride was added to an ethanol (200 ml) solution of 39.0 g (250 mmol) of 1-(4-fluoro-2-methylphenyl)ethanone (a combination of products of Wako Pure Chemical Industries, Ltd. and Tokyo Chemical Industry Co., Ltd.). The mixture was stirred at room temperature for 30 minutes. After the completion of the reaction, the reaction mixture liquid was concentrated under reduced pressure. Water was added, and the resultant mixture was extracted with ethyl acetate. The organic phase was washed with saturated brine, dried with anhydrous magnesium sulfate, and concentrated under reduced pressure. The residue was subjected to silica gel column chromatography (eluting solvent: hexane:ethyl acetate=90:10 to 69:31 (V/V)), and the fraction containing the target compound was concentrated under reduced pressure to give the title compound weighing 41.5 g (243 mmol, yield 97%) as a colorless oil.

1H-NMR spectrum (400 MHz, CDCl3) δ: 7.25-7.19 (1H, m), 7.01-6.87 (2H, m), 5.22-5.14 (1H, m), 1.88 (1H, d, J=4.3 Hz), 1.50 (3H, d, J=6.4 Hz).

Reference Example 19

(R)-1-(thiophen-3-yl)ethanol

[Chem. 57]

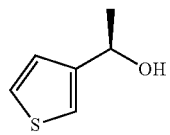

In accordance with the process described in Journal of Organic Chemistry, 72 (2007) pp. 1639-1644, 0.446 g (1.61 mmol) of (S)-5,5-diphenyl-2-methyl-3,4-propano-1,3,2-oxazaborolidine (Aldrich) was added to a tetrahydrofuran (100 ml) solution of 2.023 g (16.03 mmol) of 1-(thiophen-3-yl)ethanone (Aldrich) dried with Molecular Sieves 4A 1/16 (trade name, Wako Pure Chemical Industries, Ltd.) in an argon atmosphere at room temperature while performing stirring. Next, while controlling the temperature to around −30° C. in a dry ice-ethanol bath and while performing stirring, 19.0 ml (17.1 mmol) of 0.9 M borane-tetrahydrofuran complex (Tokyo Chemical Industry Co., Ltd.) was added dropwise over a period of 1 hour. The mixture was stirred at around −30° C. for 1 hour. After the completion of the reaction, 50 ml of water was added, and subsequently 100 ml of ethyl acetate and 5 ml of 1N hydrochloric acid were added to perform liquid separation. The organic phase was washed with 50 ml of saturated brine, dried with anhydrous magnesium sulfate, and concentrated under reduced pressure. The residue was subjected to silica gel column chromatography (eluting solvent: hexane:ethyl acetate=95:5 to 74:26 (V/V)), and the fraction containing the target compound was concentrated under reduced pressure to give the title compound weighing 1.81 g (14.1 mmol, yield 88%, optical purity 82.9% ee) as a colorless oil.

Optical Purity Analysis Conditions

Column: CHIRALCEL OJ-RH (trade name, Daicel Corporation)

Size: 0.46 cm I.D.×25 cm L.

Mobile phase: 0.03 vol % aqueous trifluoroacetic acid solution/acetonitrile=75/25 (V/V)

Flow rate: 1.0 ml/min.

Temperature: 40° C.

Wavelength: 254 nm

¹H-NMR spectrum (400 MHz, DMSO-d₆) δ: 7.44 (1H, dd, J=5.0, 3.0 Hz), 7.25 (1H, ddd, J=3.0, 1.2, 0.9 Hz), 7.07 (1H, dd, J=5.0, 1.2 Hz), 5.11 (1H, d, J=4.8 Hz), 4.80-4.71 (1H, m), 1.34 (3H, d, J=6.4 Hz).

The title compound may be obtained with an enhanced optical purity in the following manner.

At room temperature and while performing stirring, 13 g of Lipase PS Amano SD (Wako Pure Chemical Industries, Ltd.) was added to a diisopropyl ether (200 ml) solution of 13.1 g (102 mmol, optical purity 69% ee) of (R)-1-(thiophen-3-yl)ethanol synthesized in analogy to Reference Example 19 and 15.0 ml (163 mmol) of vinyl acetate. The reaction mixture liquid was stirred at 45° C. for 6.5 hours and was filtered. The filtrate was concentrated under reduced pressure. The residue was subjected to silica gel column chromatography (eluting solvent: hexane:ethyl acetate=80:20 (V/V)), and the fraction containing the target compound was concentrated under reduced pressure to give acetic acid (R)-1-(thiophen-3-yl)ethyl ester weighing 11.8 g (67 mmol, yield 65%, optical purity >99% ee) as a light yellow oil.

Optical purity analysis conditions
Column: CHIRALPAK IA (trade name, Daicel Corporation)
Size: 0.46 cm I.D.×25 cm L.
Mobile phase: hexane:2-propanol=99.5:0.5 (V/V)
Flow rate: 1.0 ml/min.
Temperature: 40° C.
Wavelength: 254 nm ¹H-NMR spectrum (400 MHz, CDCl₃) δ: 7.30 (1H, dd, J=5.0, 2.9 Hz), 7.25-7.22 (1H, m), 7.09 (1H, dd, J=5.0, 1.3 Hz), 6.00 (1H, q, J=6.6 Hz), 2.07 (3H, s), 1.56 (3H, d, J=6.5 Hz).

Under a stream of nitrogen, 2.50 g (104 mmol) of lithium hydroxide was added to an ethanol (100 ml)-water (10 ml) solution of 11.8 g of acetic acid (R)-1-(thiophen-3-yl)ethyl ester obtained above (67.1 mmol, optical purity >99% ee) at room temperature while performing stirring. The mixture was stirred at the temperature for 1.5 hours. After the completion of the reaction, the reaction mixture liquid was concentrated under reduced pressure to remove ethanol. Water was added to the residue, and the mixture was extracted with ethyl acetate. The organic phase was washed with saturated brine, dried with anhydrous magnesium sulfate, and concentrated under reduced pressure. The residue was subjected to silica gel column chromatography (eluting solvent: hexane:ethyl acetate=95:5 to 74:26 (V/V)), and the fraction containing the target compound was concentrated under reduced pressure to give the title compound weighing 8.1 g (63 mmol, yield 95%, optical purity >99.0% ee) as a light yellow oil.

Reference Example 20

(R)-1-(4-methylthiophen-3-yl)ethanol

[Chem. 58]

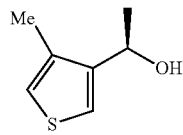

In an argon atmosphere at −30° C. to −27° C., 3.4 ml (3.1 mmol) of 0.9 M borane-tetrahydrofuran complex was added dropwise to a tetrahydrofuran (1.0 ml) solution of 78 mg (0.28 mmol) of (S)-5,5-diphenyl-2-methyl-3,4-propano-1,3,2-oxazaborolidine (Aldrich). The mixture was stirred at the temperature for 30 minutes. Next, a tetrahydrofuran (20 ml) solution of 406 mg (2.90 mmol) of 1-(4-methylthiophen-3-yl)ethanone synthesized in analogy to Reference Example 17 was added dropwise at −30° C. to −27° C., and the mixture was stirred at the temperature for 1 hour. After the completion of the reaction, water and 1N hydrochloric acid were added to the reaction mixture liquid, and the mixture was extracted with ethyl acetate. The organic phase was washed with saturated brine, dried with anhydrous magnesium sulfate, and concentrated under reduced pressure. The residue was subjected to silica gel column chromatography (eluting solvent: hexane:ethyl acetate=95:5 to 70:30 (V/V)), and the fraction containing the target compound was concentrated under reduced pressure to give the title compound weighing 387 mg (2.72 mmol, yield 94%) as a colorless oil.

Mass spectrum (EI, m/z): 142 [M]⁺.

¹H-NMR spectrum (400 MHz, CDCl₃) δ: 7.23-7.21 (1H, m), 6.92 (1H, dq, J=3.1, 0.9 Hz), 4.92 (1H, qdd, J=6.4, 4.8, 0.8 Hz), 2.27 (3H, d, J=0.9 Hz), 1.63 (1H, d, J=4.6 Hz), 1.53 (3H, d, J=6.4 Hz).

The title compound may be obtained with an enhanced optical purity in the following manner.

At room temperature and while performing stirring, 6.7 g of Lipase PS Amano SD (Wako Pure Chemical Industries, Ltd.) was added to a diisopropyl ether (67 ml) solution of 13.3 g (94 mmol, optical purity 90% ee) of (R)-1-(4-methylthiophen-3-yl)ethanol synthesized in analogy to Reference Example 20 and 16.3 ml (163 mmol) of vinyl acetate. The mixture was stirred at 45° C. for 25 hours. The reaction mixture liquid obtained was filtered, and the filtrate was concentrated under reduced pressure. The residue was subjected to silica gel column chromatography (eluting solvent: hexane:ethyl acetate=90:10 (V/V)), and the fraction containing the target compound was concentrated under reduced pressure to give acetic acid (R)-1-(4-methylthiophen-3-yl)ethyl ester weighing 10.3 g (56.0 mmol, yield 60%, optical purity >99% ee) as a light yellow oil.

Optical Purity Analysis Conditions
Column: CHIRALPAK IA (trade name, Daicel Corporation)
Size: 0.46 cm I.D.×25 cm L.
Mobile phase: hexane:2-propanol=99.5:0.5 (V/V)
Flow rate: 1.0 ml/min.
Temperature: 40° C.
Wavelength: 254 nm ¹H-NMR spectrum (400 MHz, CDCl₃) δ: 7.23 (1H, d, J=3.3 Hz), 6.94-6.90 (1H, m), 5.94 (1H, qd, J=6.5, 0.9 Hz), 2.23 (3H, d, J=1.0 Hz), 2.07 (3H, s), 1.55 (3H, d, J=6.5 Hz).

Under a stream of nitrogen, 2.0 g (84 mmol) of lithium hydroxide was added to an ethanol (50 ml)-water (5 ml) solution of 10.3 g (56.0 mmol) of acetic acid (R)-1-(4-methylthiophen-3-yl)ethyl ester obtained above at room temperature while performing stirring. The mixture was stirred at the temperature for 1.5 hours. After the completion of the reaction, the reaction mixture liquid was concentrated under reduced pressure to remove ethanol. Water was added to the residue, and the mixture was extracted with ethyl acetate. The organic phase was washed with saturated brine, dried with anhydrous magnesium sulfate, and concentrated under reduced pressure. The residue was subjected to silica gel column chromatography (eluting solvent: hexane:ethyl acetate=95:5 to 70:30 (V/V)), and the fraction containing the target compound was concentrated under reduced pressure to give the title compound weighing 7.8 g (55 mmol, yield 98%, optical purity 99.5% ee) as a colorless oil.

Optical Purity Analysis Conditions
Column: CHIRALPAK IA (trade name, Daicel Corporation)
Size: 0.46 cm I.D.×25 cm L.
Mobile phase: Liquid A:Liquid B=95:1 (V/V)
Liquid A: hexane:2-propanol=99.5:0.5 (V/V)
Liquid B: 2-propanol
Flow rate: 1.0 ml/min.
Temperature: 40° C.
Wavelength: 254 nm Reference Example 21

Acetic acid (R)-1-(2,5-difluorophenyl)ethyl ester

[Chem. 59]

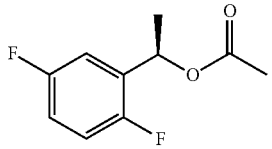

At room temperature and while performing stirring, 33 g of Lipase PS Amano SD (Wako Pure Chemical Industries, Ltd.) was added to a diisopropyl ether (200 ml) solution of 39.3 g (249 mmol) of (RS)-1-(2,5-difluorophenyl)ethanol synthesized in analogy to Reference Example 18 and 45.0 ml (450 mmol) of vinyl acetate. The mixture was stirred at 45° C. for 46.5 hours. The reaction mixture liquid obtained was filtered, and the filtrate was concentrated under reduced pressure. The residue was subjected to silica gel column chromatography (eluting solvent: hexane:ethyl acetate=90:10 (V/V)), and the fraction containing the target compound was concentrated under reduced pressure to give the title compound weighing 20.1 g (100 mmol, yield 40%, optical purity 97% ee) as a light yellow oil.

Optical Purity Analysis Conditions
Column: CHIRALPAK IA (trade name, Daicel Corporation)
Size: 0.46 cm I.D.×25 cm L.
Mobile phase: hexane:2-propanol=99.5:0.5 (V/V)
Flow rate: 1.0 ml/min.
Temperature: 40° C.
Wavelength: 254 nm
$^1$H-NMR spectrum (400 MHz, CDCl$_3$) δ: 7.11-7.05 (1H, m), 7.03-6.90 (2H, m), 6.09 (1H, q, J=6.6 Hz), 2.11 (3H, s), 1.52 (3H, d, J=6.5 Hz).

(The compound obtained in this reaction (optical purity 97% ee) was hydrolyzed in the same manner as in Reference Example 22 (optical purity 92.2% ee) and the product was treated under the same conditions as in the above reaction, thereby enhancing the optical purity.)

At room temperature and while performing stirring, 16 g of Lipase PS Amano SD (Wako Pure Chemical Industries, Ltd.) was added to a diisopropyl ether (70 ml) solution of 15.8 g (100 mmol) of (R)-1-(2,5-difluorophenyl)ethanol (optical purity 92.2% ee) and 20.0 ml (200 mmol) of vinyl acetate. The mixture was stirred at 45° C. for 64.5 hours. The reaction mixture liquid obtained was filtered, and the filtrate was concentrated under reduced pressure. The residue was subjected to silica gel column chromatography (eluting solvent: hexane:ethyl acetate=90:10 (V/V)), and the fraction containing the target compound was concentrated under reduced pressure to give the title compound weighing 19.2 g (96 mmol, yield 96%, optical purity 99.7% ee) as a light yellow oil.

Reference Example 22

(R)-1-(2,5-difluorophenyl)ethanol

[Chem. 60]

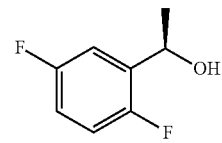

Under a stream of nitrogen, 3.5 g (150 mmol) of lithium hydroxide was added to an ethanol (100 ml)-water (10 ml) solution of 19.2 g (96 mmol, optical purity 99.7% ee) of acetic acid (R)-1-(2,5-difluorophenyl)ethyl ester synthesized in Reference Example 21 at room temperature while performing stirring. The mixture was stirred at the temperature for 1.5 hours. After the completion of the reaction, the reaction mixture liquid was concentrated under reduced pressure to remove ethanol. Water was added to the residue, and the mixture was extracted with ethyl acetate. The organic phase was washed with saturated brine, dried with anhydrous magnesium sulfate, and concentrated under reduced pressure. The residue was subjected to silica gel column chromatography (eluting solvent: hexane:ethyl acetate=90:10 to 69:31 (V/V)), and the fraction containing the target compound was concentrated under reduced pressure to give the title compound weighing 13.5 g (85.6 mmol, yield 89%, optical purity 99.0% ee) as a light yellow oil.

Optical Purity Analysis Conditions
Column: CHIRALPAK IA (trade name, Daicel Corporation)
Size: 0.46 cm I.D.×25 cm L.
Mobile phase: Liquid A:Liquid B=99:1 (V/V)
Liquid A: hexane:2-propanol=99.5:0.5 (V/V)
Liquid B: 2-propanol
Flow rate: 1.0 ml/min.
Temperature: 40° C.
Wavelength: 254 nm
$^1$H-NMR spectrum (400 MHz, CDCl$_3$) δ: 7.25-7.19 (1H, m), 7.01-6.87 (2H, m), 5.22-5.14 (1H, m), 1.88 (1H, d, J=4.3 Hz), 1.50 (3H, d, J=6.4 Hz).

Reference Example 23

(R)-1-{4'-[5-chloro-3-({[1-(thiophen-3-yl)ethoxy]carbonyl}amino)thiophen-2-yl]-[1,1'-biphenyl]-4-yl}cyclopropanecarboxylic acid ethyl ester

[Chem. 61]

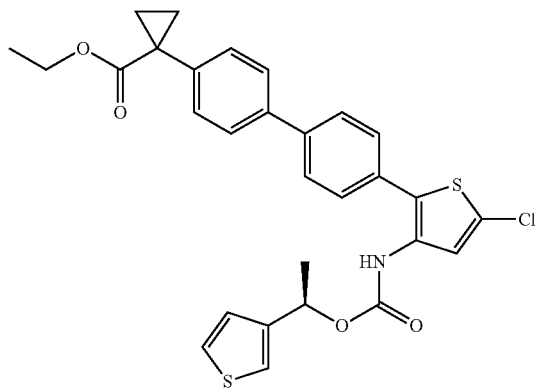

In an argon atmosphere, 340 mg (0.791 mmol) of [bis(trifluoroacetoxy)iodo]benzene was added to a toluene (6 ml) solution of 300 mg (0.704 mmol) of 1-[4'-(3-carbamoyl-5-chlorothiophen-2-yl)-[1,1'-biphenyl]-4-yl]cyclopropanecarboxylic acid ethyl ester synthesized in analogy to Reference Example 7 and 0.53 ml (6.6 mmol) of pyridine. The mixture was stirred at room temperature for 30 minutes. Next, 105 mg (0.819 mmol) of (R)-1-(thiophen-3-yl)ethanol synthesized in analogy to Reference Example 19 was added in an argon atmosphere at room temperature, and the mixture was stirred for 2 hours while performing heating at 70° C. After the completion of the reaction, ethyl acetate and water were added to the reaction mixture liquid, and the organic phase was separated. The organic phase was washed with saturated brine, dried with anhydrous magnesium sulfate, and concentrated under reduced pressure. The residue was subjected to silica gel column chromatography (eluting solvent: hexane:ethyl acetate=80:20 to 30:70 (V/V)), and the fraction containing the target compound was concentrated under reduced pressure to give the title compound weighing 306 mg (0.55 mmol, yield 79%) as a brown oil.

Mass spectrum (DUIS$^+$, m/z): 550 [M−1]$^-$.

$^1$H-NMR spectrum (400 MHz, CDCl$_3$) δ: 7.69-7.63 (2H, m), 7.63-7.51 (3H, m), 7.48-7.40 (4H, m), 7.31 (1H, dd, J=5.0, 2.9 Hz), 7.28-7.26 (1H, m), 7.11 (1H, dd, J=5.0, 1.3 Hz), 6.72 (1H, s), 5.99 (1H, q, J=6.6 Hz), 4.13 (2H, q, J=7.1 Hz), 1.64 (2H, dd, J=7.0, 4.0 Hz), 1.62 (3H, d, J=6.5 Hz), 1.23 (2H, dd, J=7.0, 4.0 Hz), 1.19 (3H, t, J=7.1 Hz).

Reference Example 24

(R)-1-[4'-(5-chloro-3-{[(1-phenylethoxy)carbonyl]amino}thiophen-2-yl)-2'-methoxy[1,1'-biphenyl]-4-yl]cyclopropanecarboxylic acid ethyl ester

[Chem. 62]

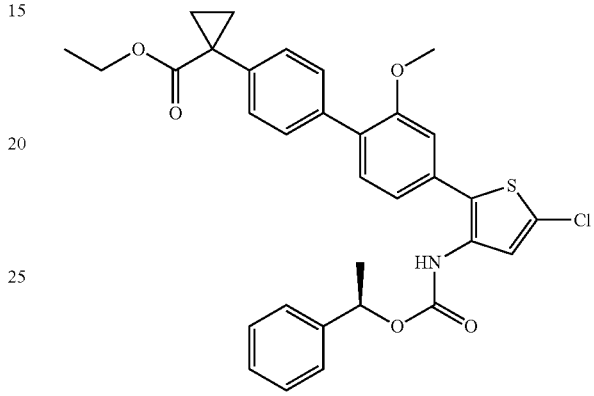

In a nitrogen atmosphere at room temperature, 2.4 g (5.6 mmol) of [bis(trifluoroacetoxy)iodo]benzene was added to a toluene (20 ml) solution of 2.0 g (4.4 mmol) of 1-[4'-(3-carbamoyl-5-chlorothiophen-2-yl)-2'-methoxy-[1,1'-biphenyl]-4-yl]cyclopropanecarboxylic acid ethyl ester synthesized in analogy to Reference Example 8, 0.80 g (6.6 mmol) of (R)-1-phenylethanol (Tokyo Chemical Industry Co., Ltd.) and 1.2 ml (15 mmol) of pyridine. The mixture was stirred for 1.5 hours while performing heating at 60° C. After the completion of the reaction, the reaction mixture liquid was concentrated under reduced pressure. The residue was subjected to silica gel column chromatography (eluting solvent: hexane:ethyl acetate=99:1 to 80:20 (V/V)), and the fraction containing the target compound was concentrated under reduced pressure to give the title compound weighing 1.46 g (4.0 mmol (purity 72 wt %), yield 42%) as an orange oil.

Mass spectrum (CI, m/z): 575 [M]$^+$.

$^1$H-NMR spectrum (400 MHz, DMSO-d$_6$) δ: 9.39 (1H, brs), 7.40-7.26 (10H, m), 7.23-7.16 (2H, m), 7.10 (1H, dd, J=7.8, 1.6 Hz), 5.75 (1H, q, J=6.4 Hz), 4.06 (2H, q, J=7.1 Hz), 3.73 (3H, s), 1.56-1.41 (5H, m), 1.23 (2H, dd, J=7.0, 4.0 Hz), 1.13 (3H, t, J=7.0 Hz).

Reference Example 25

(R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylic acid 2-(trimethylsilyl)ethyl ester

[Chem. 63]

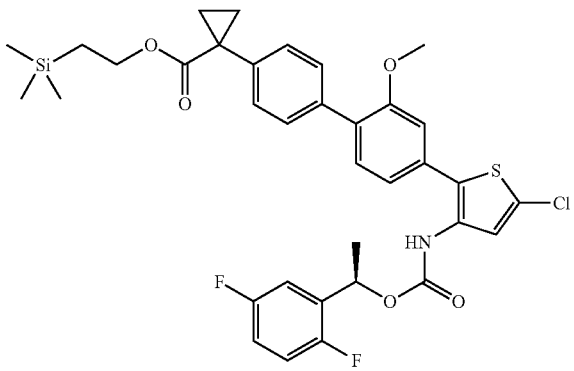

In an argon atmosphere at room temperature, 874 mg (2.03 mmol) of [bis(trifluoroacetoxy)iodo]benzene was added to a toluene (10 ml) solution of 886 mg (1.68 mmol) of 1-[4'-(3-carbamoyl-5-chlorothiophen-2-yl)-2'-methoxy-[1,1'-biphenyl]-4-yl]cyclopropanecarboxylic acid 2-(trimethylsilyl)ethyl ester synthesized in analogy to Reference Example 16 and 0.65 ml (8.0 mmol) of pyridine. The mixture was stirred for 5 minutes. Thereafter, 413 mg (2.61 mmol) of (R)-1-(2,5-difluorophenyl)ethanol (Enamine) was added. The mixture was stirred for 1 hour while performing heating at a bath temperature of 70° C. After the completion of the reaction, water and ethyl acetate were added to the reaction mixture liquid, and the mixture was extracted with ethyl acetate. The organic phase was dried with anhydrous magnesium sulfate and was concentrated under reduced pressure. The residue was subjected to silica gel column chromatography (eluting solvent: hexane:ethyl acetate=99:1 to 94:6 (V/V)), and the fraction containing the target compound was concentrated under reduced pressure to give the title compound weighing 1.16 g (1.46 mmol (purity 86 wt %), yield 87%) as a brown oil (semisolid).

Mass spectrum (DUIS⁻, m/z): 682 [M−1]⁻.

¹H-NMR spectrum (400 MHz, DMSO-d$_6$) δ: 9.55 (1H, brs), 7.45-7.40 (2H, m), 7.39-7.17 (8H, m), 7.10 (1H, dd, J=7.9, 1.5 Hz), 5.91 (1H, q, J=6.3 Hz), 4.14-4.07 (2H, m), 3.76 (3H, s), 1.55-1.42 (3H, m), 1.49 (2H, dd, J=6.8, 3.9 Hz), 1.23 (2H, dd, J=7.0, 4.0 Hz), 0.91-0.84 (2H, m), −0.05 (9H, s).

Reference Example 26

(R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylic acid ethyl ester

[Chem. 64]

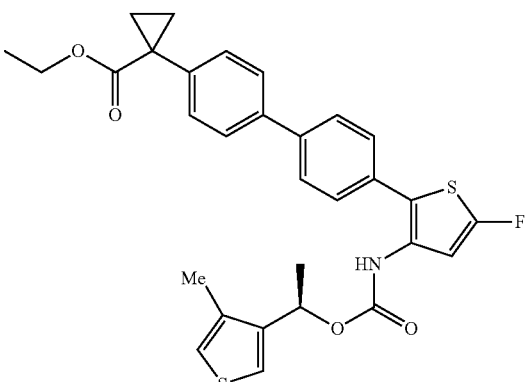

In an argon atmosphere, 0.24 ml (1.7 mmol) of triethylamine and 0.29 ml (1.4 mmol) of diphenylphosphoryl azide were added to a toluene (10 ml) solution of 456 mg (1.11 mmol) of 2-{4'-[1-(ethoxycarbonyl)cyclopropyl]-[1,1'-biphenyl]-4-yl}-5-fluorothiophene-3-carboxylic acid synthesized in analogy to Reference Example 13. The mixture was stirred at room temperature for 30 minutes. Next, there was added a toluene (1 ml) solution of 190 mg (1.34 mmol) of (R)-1-(4-methylthiophen-3-yl)ethanol that had been synthesized in analogy to Reference Example 20 and had been dried with Molecular Sieves 4A (powder) (trade name, NACALAI TESQUE, INC.) (0.3 g). The resultant mixture was stirred for 2 hours while performing heating at 70° C. After the completion of the reaction, ethyl acetate and a saturated aqueous ammonium chloride solution were added to the reaction mixture liquid, and the organic phase was separated. The organic phase was washed with saturated brine, dried with anhydrous magnesium sulfate, and concentrated under reduced pressure. The residue was subjected to silica gel column chromatography (eluting solvent: hexane:ethyl acetate=80:20 (V/V)), and the fraction containing the target compound was concentrated under reduced pressure to give the title compound weighing 570 mg (1.04 mmol, yield 93%) as a colorless oil.

Mass spectrum (DUIS⁻, m/z): 548 [M−1]⁻.

¹H-NMR spectrum (400 MHz, DMSO-d$_6$) δ: 9.31 (1H, brs), 7.74-7.68 (2H, m), 7.66-7.61 (2H, m), 7.57-7.40 (5H, m), 7.17-7.13 (1H, m), 6.83 (1H, brs), 5.74 (1H, q, J=6.5 Hz), 4.05 (2H, q, J=7.2 Hz), 2.17 (3H, brs), 1.60-1.43 (3H, m), 1.51 (2H, dd, J=6.8, 4.0 Hz), 1.23 (2H, dd, J=7.1, 4.1 Hz), 1.11 (3H, t, J=7.1 Hz).

Reference Example 27

(R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylic acid ethyl ester

[Chem. 65]

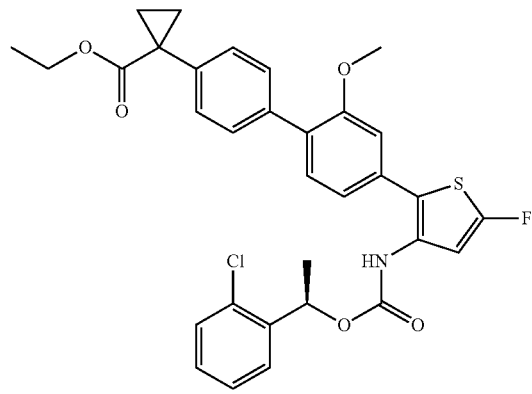

In an argon atmosphere, 0.040 ml (0.29 mmol) of triethylamine and 0.045 ml (0.21 mmol) of diphenylphosphoryl azide were added to a toluene (4.0 ml) solution of 72 mg (0.16 mmol) of 2-{4'-[1-(ethoxycarbonyl)cyclopropyl]-2-methoxy-[1,1'-biphenyl]-4-yl}-5-fluorothiophene-3-carboxylic acid synthesized in analogy to Reference Example 14. The mixture was stirred at room temperature for 30 minutes. Next, there was added 35 mg (0.22 mmol) of (R)-1-(2-chlorophenyl)ethanol (Shanghai AoBo Bio-pharm). The mixture was stirred for 2 hours while performing heating at 70° C. After the completion of the reaction, ethyl acetate and water were added to the reaction mixture liquid, and the organic phase was separated. The organic phase was washed with saturated brine, dried with anhydrous magnesium sulfate, and concentrated under reduced pressure. The residue was subjected to silica gel column chromatography (eluting solvent: hexane:ethyl acetate=93:7 to 72:28 (V/V)), and the fraction containing the target compound was concentrated under reduced pressure to give the title compound weighing 84 mg (0.061 mmol (purity 43 wt %), yield 37%) as a colorless oil.

Mass spectrum (EI, m/z): 593 [M]+.

$^1$H-NMR spectrum (400 MHz, CDCl$_3$) δ: 7.52-7.48 (2H, m), 7.43-7.17 (9H, m), 7.06 (1H, dd, J=7.8, 1.6 Hz), 6.97 (1H, d, J=1.6 Hz), 6.23 (1H, q, J=6.7 Hz), 4.13 (2H, q, J=7.1 Hz), 3.82 (3H, s), 1.63 (2H, dd, J=6.9, 3.9 Hz), 1.57 (3H, d, J=6.7 Hz), 1.24 (2H, dd, J=7.0, 4.0 Hz), 1.20 (3H, t, J=7.2 Hz).

Reference Example 28

(R)-1-{4'-[5-chloro-3-({[1-(thiophen-3-yl)ethoxy]carbonyl}amino)thiophen-2-yl]-[1,1'-biphenyl]-4-yl}cyclopropanecarboxylic acid

[Chem. 66]

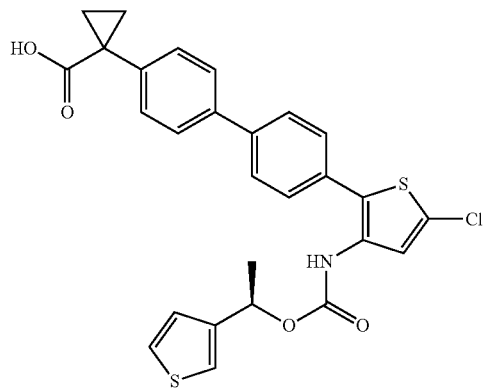

2.0 ml (4.0 mmol) of a 2N aqueous sodium hydroxide solution was added to a 2-propanol (4 ml) solution of 304 mg (0.551 mmol) of (R)-1-{4'-[5-chloro-3-({[1-(thiophen-3-yl)ethoxy]carbonyl}amino)thiophen-2-yl]-[1,1'-biphenyl]-4-yl}cyclopropanecarboxylic acid ethyl ester synthesized in analogy to Reference Example 23. The mixture was stirred at room temperature for 42.5 hours. After the completion of the reaction, the reaction mixture liquid was acidified by the addition of 2N hydrochloric acid, and was extracted with ethyl acetate. The organic phase was washed sequentially with water and saturated brine, dried with anhydrous magnesium sulfate, and concentrated under reduced pressure. The residue was subjected to silica gel column chromatography (COOH column, eluting solvent: hexane:ethyl acetate=70:30 to 10:90 (V/V)), and the fraction containing the target compound was concentrated under reduced pressure. Hexane (10 ml) and ethyl acetate (3 ml) were added to the residue. The white solid precipitated was filtered off and was washed with a hexane-ethyl acetate (3:1 (V/V)) mixed solution. The mother liquor and the washings were concentrated under reduced pressure to give the title compound weighing 65 mg (0.55 mmol, yield 23%) as a white solid.

Mass spectrum (DUIS−, m/z): 522 [M−1]−.

$^1$H-NMR spectrum (400 MHz, DMSO-d$_6$) δ: 12.37 (1H, brs), 9.33 (1H, brs), 7.74-7.68 (2H, m), 7.65-7.60 (2H, m), 7.58-7.50 (3H, m), 7.48-7.37 (3H, m), 7.25-7.07 (2H, m), 5.82 (1H, q, J=6.4 Hz), 1.56-1.44 (3H, m), 1.48 (2H, dd, J=6.7, 3.8 Hz), 1.19-1.16 (2H, m).

Reference Example 29

(R)-1-[4'-(5-chloro-3-{[(1-phenylethoxy)carbonyl]amino}thiophen-2-yl)-2'-methoxy-[1,1'-biphenyl]-4-yl]cyclopropanecarboxylic acid

[Chem. 67]

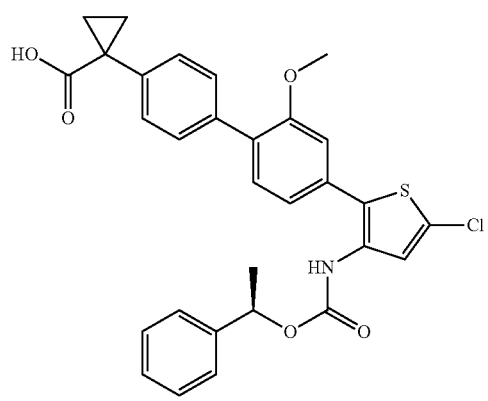

8.0 ml (16.0 mmol) of a 2N aqueous sodium hydroxide solution was added to a 2-propanol (30 ml) solution of 1.46 g (4.0 mmol (purity 72 wt %)) of (R)-1-[4'-(5-chloro-3-{[(1-phenylethoxy)carbonyl]amino}thiophen-2-yl)-2'-methoxy-[1,1'-biphenyl]-4-yl]cyclopropanecarboxylic acid ethyl ester synthesized in Reference Example 24. The mixture was stirred at room temperature for 110 hours. After the completion of the reaction, the reaction mixture liquid was acidified by the addition of 2N hydrochloric acid, and was extracted with methylene chloride. The organic phase was washed with saturated brine, dried with anhydrous magnesium sulfate, and concentrated under reduced pressure. The residue was subjected to silica gel column chromatography (eluting solvent: hexane:ethyl acetate=80:20 to 0:100 (V/V)), and the fraction containing the target compound was concentrated under reduced pressure. The residue was dissolved in a small amount of ethanol. Water was added to the solution to precipitate a solid. The solid was collected by filtration, washed with water, and dried by vacuum heating to give the title compound weighing 588 mg (1.07 mmol, yield 58%) as a light red solid.

Mass spectrum (DUIS$^-$, m/z): 546 [M−1]$^-$.

$^1$H-NMR spectrum (400 MHz, DMSO-d$_6$) δ: 12.34 (1H, brs), 9.40 (1H, brs), 7.45-7.25 (10H, m), 7.21-7.16 (2H, m), 7.09 (1H, dd, J=7.9, 1.6 Hz), 5.75 (1H, q, J=6.4 Hz), 3.73 (3H, s), 1.54-1.41 (5H, m), 1.18-1.12 (2H, m).

Reference Example 30

(R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylic acid

[Chem. 68]

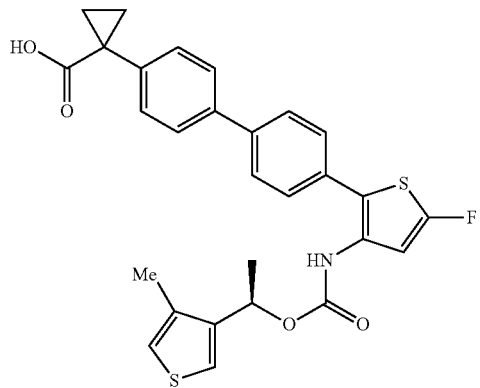

4.0 ml (8.0 mmol) of a 2N aqueous sodium hydroxide solution was added to a 2-propanol (12 ml) solution of 565 mg (1.03 mmol) of (R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylic acid ethyl ester synthesized in analogy to Reference Example 26. The mixture was stirred at room temperature for 91 hours. After the completion of the reaction, the reaction mixture liquid was acidified by the addition of 1N hydrochloric acid, and was extracted with methylene chloride. The organic phase was washed sequentially with water and saturated brine, dried with anhydrous magnesium sulfate, and concentrated under reduced pressure. The residue was subjected to silica gel column chromatography (eluting solvent: hexane:ethyl acetate=50:50 (V/V)), and the fraction containing the target compound was concentrated under reduced pressure. Next, 6 ml of hexane and 12 ml of ethyl acetate were added, and the mixture was heated at 50° C. and was cooled. The solid precipitated was filtered off and was washed with a hexane-ethyl acetate (50:50 (V/V)) mixed solution. The mother liquor and washings were concentrated under reduced pressure. To the residue were added 8 ml of acetonitrile, 4 ml of water and 3 ml of tetrahydrofuran. Freeze drying of the mixture resulted in the title compound weighing 193 mg (0.37 mmol, yield 36%) as a white solid.

Mass spectrum (DUIS$^-$, m/z): 520 [M−1]$^-$.

$^1$H-NMR spectrum (400 MHz, DMSO-d$_6$) δ: 12.38 (1H, brs), 9.33 (1H, brs), 7.73-7.67 (2H, m), 7.65-7.59 (2H, m), 7.57-7.50 (2H, m), 7.49-7.38 (3H, m), 7.19-7.12 (1H, m), 6.83 (1H, brs), 5.74 (1H, q, J=6.4 Hz), 2.17 (3H, brs), 1.59-1.44 (3H, m), 1.48 (2H, dd, J=6.7, 3.8 Hz), 1.18 (2H, dd, J=6.9, 3.9 Hz).

Reference Example 31

(R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylic acid

[Chem. 69]

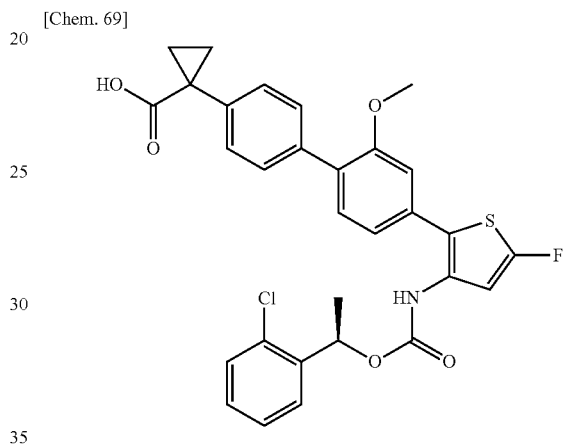

1.5 ml (3.0 mmol) of a 2N aqueous sodium hydroxide solution was added to a 2-propanol (3.0 ml) solution of 80 mg (0.058 mmol (purity 43 wt %)) of (R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylic acid ethyl ester synthesized in Reference Example 27. The mixture was stirred at room temperature for 23 hours. After the completion of the reaction, the reaction mixture liquid was acidified by the addition of 2N hydrochloric acid, and was extracted with methylene chloride. The organic phase was washed sequentially with water and saturated brine, dried with anhydrous magnesium sulfate, and concentrated under reduced pressure. The residue was subjected to silica gel column chromatography (COOH column, eluting solvent: hexane:ethyl acetate=80:20 to 20:80 (V/V)), and the fraction containing the target compound was concentrated under reduced pressure to give the title compound weighing 13 mg (0.023 mmol, yield 40%) as a white solid.

Mass spectrum (DUIS$^-$, m/z): 564 [M−1]$^-$.

$^1$H-NMR spectrum (400 MHz, DMSO-d$_6$) δ: 12.35 (1H, brs), 9.55 (1H, brs), 7.60-7.28 (9H, m), 7.18 (1H, d, J=1.5 Hz), 7.09 (1H, dd, J=7.8, 1.4 Hz), 6.84 (1H, d, J=2.5 Hz), 6.00 (1H, q, J=6.1 Hz), 3.77 (3H, s), 1.55-1.39 (5H, m), 1.21-1.10 (2H, m).

Reference Example 32

(R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylic acid

[Chem. 70]

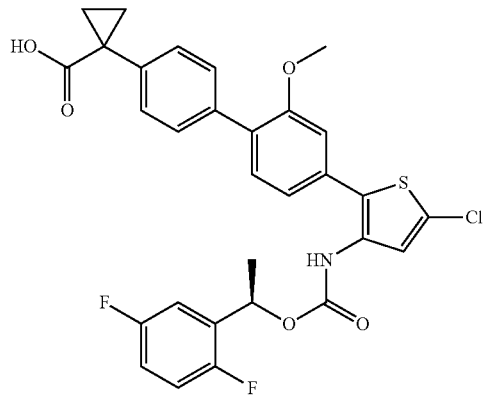

In an argon atmosphere at room temperature, 9.0 ml (9.0 mmol) of a 1 M tetrahydrofuran solution of tetrabutylammonium fluoride was added to a dimethylformamide (90 ml) solution of 3.00 g (4.38 mmol) of (R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylic acid 2-(trimethylsilyl)ethyl ester synthesized in analogy to Reference Example 25. The mixture was stirred at the temperature for 2 hours. After the completion of the reaction, ethyl acetate and water were added to the reaction mixture liquid, and the pH was adjusted to approximately 3 with 0.5N hydrochloric acid. The reaction mixture liquid was separated into phases. The organic phase was washed sequentially with water and saturated brine, dried with anhydrous magnesium sulfate, and concentrated under reduced pressure. 2-Propanol (40 ml) and water (40 ml) were added to the residue, and the mixture was ultrasonicated. The solid precipitated was filtered off and was washed with water. Thus, a crude title compound weighing 2.86 g was obtained. The crude compound was subjected to silica gel column chromatography (eluting solvent: hexane:ethyl acetate=70:30 to 10:90 (V/V)), and the fraction containing the target compound was concentrated under reduced pressure. Heptane was added to the residue, and the solid precipitated was filtered off. Thereby, the title compound weighing 1.62 g (2.77 mmol, yield 63%) was obtained as a white solid.

Mass spectrum (DUIS$^-$, m/z): 582 [M−1]$^-$.

$^1$H-NMR spectrum (400 MHz, DMSO-d$_6$) δ: 12.35 (1H, brs), 9.54 (1H, brs), 7.44-7.39 (2H, m), 7.39-7.19 (7H, m), 7.18 (1H, d, J=1.6 Hz), 7.10 (1H, dd, J=7.9, 1.6 Hz), 5.91 (1H, q, J=6.5 Hz), 3.76 (3H, s), 1.56-1.43 (3H, m), 1.47 (2H, dd, J=6.7, 3.7 Hz), 1.18 (2H, dd, J=6.8, 4.0 Hz).

Test Example 1

Test of Binding of GTPγS to LPA1 Receptor

5 μg of a membrane fraction of RH 7777 cells expressing human LPA1 receptor (A324, ChanTest) is suspended in a reaction buffer (20 mM HEPES, 100 mM NaCl, 10 mM MgCl$_2$, 10 μM GDP, 5 μg saponin, 0.2% BSA, 0.1 nM [$^{35}$S]GTPγS (NEG030X, Perkin Elmer), pH 7.4). The test compounds dissolved in DMSO in various concentrations are each added to the suspension. After preincubation at 30° C. for 15 minutes, LPA (L7260, Sigma, final concentration 100 nM) is added, and the suspensions are incubated at 30° C. for 30 minutes. The membrane fractions are collected on a glass fiber filter (GF/B, Whatman) by using a cell harvester (M30, Brandel), and are washed with a 10 mM phosphate buffer (pH 7.4). The radioactivity of the membrane fractions is measured with a liquid scintillation analyzer (2900TR, Packard) and the concentration (IC$_{50}$) of the test compound required for 50% inhibition of the binding of the LPA1 receptor and [$^{35}$S]GTPγS is determined by non-linear regression analysis using EXSAS (version 7.6.0, Arm Systex).

Test Example 2

Cell Migration Test

The cell migration test was carried out using Chemo-Tx (registered trademark) (116-8, Neuro Probe). A2058 human melanoma cells (obtained from European Collection of Cell Culture) were cultured in a serum-free EMEM medium for 24 hours, and were re-suspended in a 0.1% BSA-containing DMEM medium to give a cell suspension. The test compounds dissolved in DMSO in various concentrations were each added to the cell suspension, and the suspensions were cultured at 37° C. for 15 minutes (final DMSO concentration 0.5%). LPA dissolved in a 0.1% BSA-containing DMEM medium (final concentration 100 nM) was added to a Chemo-Tx 96 well plate, and a Chemo-Tx filter coated with 0.001% Fibronectin on both sides was placed onto the plate. The cultured cell suspensions (25,000 cells) were added onto the upper surface of the filter and were further cultured at 37° C. for 3 hours. Thereafter, the cells on the upper surface of the filter were removed. After the filter was removed and was dried, the cells which had migrated to the lower surface of the filter were stained with Diff-Quik stain (16920, Sysmex). The absorbance of the filter (570 nm) was measured and the concentration (IC$_{50}$) of the test compound required for 50% inhibition of the cell migration activity of LPA was determined by non-linear regression analysis using EXSAS (version 7.6.0, Arm Systex).

In this test, the compounds of the present invention showed excellent activity. For example, the IC$_{50}$ values of the compounds of Examples 1 to 15 were not more than 200 nM.

Test Example 3

LPA-Induced Histamine Release Test in Mice

The LPA-induced histamine release test in mice was carried out in accordance with the method by Swaney et al. (The Journal of Pharmacology and Experimental Therapeutics, 336 (2011), pp. 693-700). The test compound was suspended in a 0.5% methylcellulose solution (133-14255, Wako Pure Chemical Industries, Ltd.), and orally administered to male CD1 mice (body weight 30 to 40 g, supplied by Charles River Laboratories Japan) at a dose of 10 ml/kg. 4 hours after the administration, LPA (857130P, Avanti) dissolved in 0.1% BSA-containing PBS was administered via the tail vein (300 μg/mouse). Immediately thereafter, each of the mice was anesthetized with isoflurane, and blood was collected from a vein 2 minutes after the administration of LPA. The blood was placed into a test tube containing EDTA, and was centrifuged at 4° C., 2,000× g for 10 minutes to give plasma.

The histamine concentration in the plasma was measured with an EIA kit (62HTMPEB, Cisbio Bioassays).

The inhibition rate (%) in 0.5% methylcellulose solution administration group was calculated in each individual based on the plasma histamine concentration in the mouse to which the test compound had been administered, and the rate of individuals which showed the inhibition rate of 80% or more was expressed as the efficacy rate (%).

In this test, the compounds of the present invention showed excellent activity. For example, the compounds of Examples 1 to 15 achieved 50% or more efficacy rate at a dose of 10 mg/kg.

Test Example 4

Bleomycin-Induced Pulmonary Fibrosis Models

Bleomycin hydrochloride (Nippon Kayaku Co., Ltd.) was administered to mice to prepare pulmonary fibrosis models. The test compound was orally administered every day from the day on which the bleomycin administration was started. On Day 3 to Day 42 after the bleomycin treatment, bronchoalveolar lavage fluids (BALFs) or lungs were collected under anesthesia with isoflurane. The BALFs were centrifuged at 800× g for 10 minutes to give supernatants. The supernatants were analyzed with DC protein assay kit (500-0114, Biorad) to determine the amounts of protein, and were analyzed with Sircol soluble collagen assay kit (S111, Biocolor) to determine the amounts of collagen. Further, biomarkers for inflammation and fibrosis in the supernatants were measured by the ELISA method. Regarding the lungs, after their wet weights were measured, the amounts of hydroxyproline in the tissues were measured by a modification of the Woessner method (Archives of Biochemistry and Biophysics, 93 (1961), pp. 440-447). Portions of the lungs were fixed in 10% formalin neutral buffer solution and were observed for histopathological changes. The results were statistically analyzed using EXSAS (version 7.6.0, Arm Systex).

Test Example 5

Unilateral Ureteral Obstruction (UUO) Renal Fibrosis Models

The abdomen of mice anesthetized with isoflurane is incised. The left ureter is ligated with a silk thread to prepare UUO models. The test compound is orally administered every day from the day on which the UUO models are prepared. On Day 8, Day 14 or Day 21 after the UUO model preparation, the kidneys are harvested and their wet weights are measured. RNA is extracted from portions of the kidneys and the expression levels of the fibrosis marker genes are measured by the quantitative PCR method. Further, the amounts of hydroxyproline or collagen in the renal tissues are measured. The results are statistically analyzed using EXSAS.

Test Example 6

Carbon Tetrachloride ($CCl_4$)-Induced Hepatic Fibrosis Models

Diluted $CCl_4$ (035-01273, Wako Pure Chemical Industries, Ltd.) is administered to mice twice a week to prepare hepatic fibrosis models. The test compound is orally administered every day from the day on which the $CCl_4$ administration is started. On Day 3 to Day 28 after the start of the $CCl_4$ administration, the livers are collected under anesthesia with isoflurane, and their wet weights are measured. RNA is extracted from portions of the livers, and the expression levels of the fibrosis marker genes are measured by the quantitative PCR method. Further, the amounts of hydroxyproline or collagen in the hepatic tissues are measured. Portions of the livers are fixed in 10% formalin neutral buffer solution, and are observed for histopathological changes. The results are statistically analyzed using EXSAS.

Test Example 7

Non-Alcoholic Steatohepatitis (NASH) Rat Models

NASH models are prepared by feeding rats with a methionine/choline-deficient (MCD) diet. The rats are allowed to freely take a regular diet or the MCD diet for 20 weeks. The test compound is orally administered every day from the day on which the feeding with the MCD diet is started. After the breeding for 20 weeks, the livers are collected under anesthesia with isoflurane, and their wet weights are measured. RNA is extracted from portions of the livers, and the expression levels of the fibrosis marker genes are measured by the quantitative PCR method. Further, the amounts of hydroxyproline or collagen in the hepatic tissues are measured. Portions of the livers are fixed in 10% formalin neutral buffer solution, and are observed for histopathological changes. The results are statistically analyzed using EXSAS.

Test Example 8

Non-Alcoholic Steatohepatitis (NASH) Mouse Models

STAM (registered trademark) mice (available from Stelic Institute & Co., Inc.) are used as NASH models. The STAM (registered trademark) mice are prepared by subcutaneously administering 200 μg of streptozotocin (Sigma Aldrich) one time to the back of 2-day old male mice and feeding the mice with a high fat diet (High Fat Diet 32, CLEA Japan, Inc.) after 4 weeks after birth (Medical Molecular Morphology, 46 (2013) pp. 141-152).

The test compound is orally administered every day after 5 or 6 weeks after birth. At the age of 9 or 10 weeks, bloods and livers are collected under anesthesia. The bloods are subjected to biochemical tests. After the wet weights of the livers are measured, RNA is extracted from portions of the livers, and the expression levels of the inflammation and fibrosis marker genes are measured by the quantitative PCR method. Further, the amounts of hydroxyproline or collagen in the hepatic tissues are measured. Paraffin sections or frozen sections are prepared from portions of the livers and are subjected to histopathological tests to determine the NAFLD activity scores, the fibrosis areas or inflammation areas. The results are statistically analyzed using EXSUS (version 8.0, CAC EXICARE CORPORATION) or Prism 4 (GraphPad Software, Inc.).

Test Example 9

Non-Alcoholic Steatohepatitis (NASH) Mouse Models

NASH models are prepared by breeding mice with a choline-deficient, 0.1% methionine-containing high fat diet (A06071302, Research Diets, Inc.) (International Journal of Experimental Pathology, 94 (2013) pp. 93-103).

The test compound is orally administered every day from the day on which the feeding with the CDAHFD is started. After 8 to 12 weeks, livers are collected under anesthesia with isoflurane and their wet weights are measured. RNA is extracted from portions of the livers, and the expression levels of the inflammation and fibrosis marker genes are measured by the quantitative PCR method. Further, the amounts of hydroxyproline or collagen in the hepatic tissues are measured. Portions of the livers are fixed in 10% formalin neutral buffer solution and are observed for histopathological changes. The results are statistically analyzed using EXSUS (version 8.0, CAC EXICARE CORPORATION).

Test Example 10

Pharmacokinetic Studies in Monkeys

A disposable catheter was inserted from a nasal cavity into the stomach of a Cynomolgus monkey deprived of food from the evening of the day before the test. Through a syringe tube, a 0.5% methylcellulose suspension or solution containing the test compound at 10 mg/2 ml was orally administered one time at a dose of 2 ml/kg. Through a syringe tube, blood was sampled from the femoral vein before the administration, and 15 minutes, 30 minutes, 1 hour, 2 hours, 4 hours, 8 hours, 12 hours and 24 hours after the administration. EDTA-2K was added to the blood samples, and the samples were centrifuged (4° C., 1710× g, 3000 rpm, 15 minutes) to give plasmas. The plasmas were deproteinized by the addition of acetonitrile (50 μL plasma+ 200 μL acetonitrile mixture) and the mixtures were filtered (PTFE, 0.2 μm). The filtrates were analyzed with LC-MS/MS (3200 QTrap, AB SCIEX; and LC-20A or LC-30A series, Shimadzu Corporation) to determine the concentrations of the test compound in the plasmas. The AUC (the area under the plasma concentration curve) was calculated with Phoenix WinNonlin (CERTARA) based on the changes in the concentration in the plasma.

From the results of Test Examples 2 and 3, the α-halogen-substituted thiophene compound salts of the present invention have an LPA receptor antagonistic action and are particularly useful as medicaments for the treatment and/or the prevention (preferably, medicaments for the treatment) of diseases accompanying fibrosis, immunological or inflammatory diseases, central or peripheral nervous system diseases, urologic diseases and cancer-related diseases.

Preparation Example 1

Hard Capsules

Standard two-piece hard gelatin capsules are loaded with a powder (100 mg) of the compound salt of the Example, lactose (150 mg), cellulose (50 mg) and magnesium stearate (6 mg) to give hard capsules, which are washed and then dried.

Preparation Example 2

Soft Capsules

A mixture of a digestible oil such as soybean oil or olive oil and the compound salt of the Example is injected into gelatin to give soft capsules containing 100 mg of the active ingredient, and the soft capsules are washed and then dried.

Preparation Example 3

Tablets

In accordance with a method known in the pharmaceutical field, tablets are produced using the compound salt (100 mg) of the Examples, colloidal silicon dioxide (0.2 mg), magnesium stearate (0.2 mg), microcrystalline cellulose (0.2 mg), starch (0.2 mg) and lactose (98.8 mg). The tablets may be coated as required.

INDUSTRIAL APPLICABILITY

The α-halogen-substituted thiophene compound salts of the invention represented by the general formula (I) have a potent LPA receptor antagonistic action and excellent properties such as long-lasting medicinal effects and solubility, and are useful as medicaments (medicaments for the treatment and/or the prevention of diseases accompanying fibrosis, immunological or inflammatory diseases, central or peripheral nervous system diseases, urologic diseases and cancer-related diseases).

The invention claimed is:

1. A salt of formula (I):

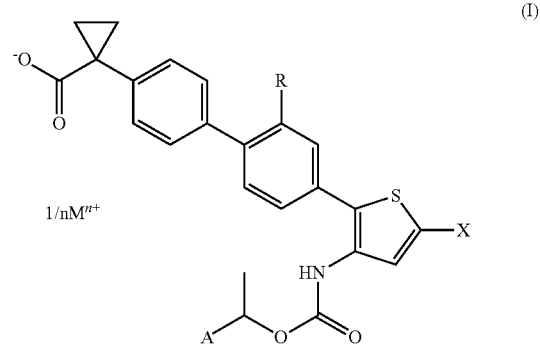

wherein
R is a hydrogen atom or a methoxy group,
X is a halogen atom,
A is selected from the group consisting of:

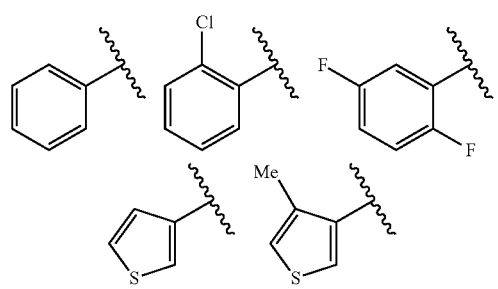

M is an alkali metal or an alkaline earth metal, and
n is 1 when M is an alkali metal and is 2 when M is an alkaline earth metal.

2. The salt according to claim 1, wherein the alkali metal or the alkaline earth metal is sodium, potassium or calcium.

3. A salt of (R)-1-[4'-(5-chloro-3-{[(1-phenylethoxy)carbonyl]amino}thiophen-2-yl)-2'-methoxy[1,1'-biphenyl]-4-yl]cyclopropanecarboxylic acid with an alkali metal or an alkaline earth metal.

4. The salt according to claim 3, wherein the alkali metal or the alkaline earth metal is sodium, potassium or calcium.

5. A salt of (R)-1-{4'-[5-chloro-3-({[1-(2,5-difluorophenyl)ethoxy]carbonyl}amino)thiophen-2-yl]-2'-methoxy-[1,1'-biphenyl]-4-yl}cyclopropanecarboxylic acid with an alkali metal or an alkaline earth metal.

6. The salt according to claim 5, wherein the alkali metal or the alkaline earth metal is sodium, potassium or calcium.

7. A salt of (R)-1-{4'-[3-({[1-(2-chlorophenyl)ethoxy]carbonyl}amino)-5-fluorothiophen-2-yl]-2'-methoxy-[1,1'-biphenyl]-4-yl}cyclopropanecarboxylic acid with an alkali metal or an alkaline earth metal.

8. The salt according to claim 7, wherein the alkali metal or the alkaline earth metal is sodium, potassium or calcium.

9. A salt of (R)-1-{4'-[5-chloro-3-({[1-(thiophen-3-yl)ethoxy]carbonyl}amino)thiophen-2-yl]-[1,1'-biphenyl]-4-yl}cyclopropanecarboxylic acid with an alkali metal or an alkaline earth metal.

10. The salt according to claim 9, wherein the alkali metal or the alkaline earth metal is sodium, potassium or calcium.

11. A salt of (R)-1-{4'-[5-fluoro-3-({[1-(4-methylthiophen-3-yl)ethoxy]carbonyl}amino)thiophen-2-yl]-[1,1'-biphenyl]-4-yl}cyclopropanecarboxylic acid with an alkali metal or an alkaline earth metal.

12. The salt according to claim 11, wherein the alkali metal or the alkaline earth metal is sodium, potassium or calcium.

13. An LPA receptor antagonist comprising the salt according to claim 1 as an active ingredient.

14. A pharmaceutical composition comprising the salt according to claim 1 as an active ingredient.

15. The pharmaceutical composition according to claim 14 for the treatment of fibrosis, rheumatoid arthritis or cancer.

* * * * *